United States Patent
Nacharaju et al.

(10) Patent No.: US 10,028,918 B2
(45) Date of Patent: Jul. 24, 2018

(54) NANOPARTICLE DELIVERY VEHICLE FOR S-NITROSO-N-ACETYL CYSTEINE AND USES THEREOF

(71) Applicant: ALBERT EINSTEIN COLLEGE OF MEDICINE, INC., Bronx, NY (US)

(72) Inventors: Parimala Nacharaju, Staten Island, NY (US); Adam J. Friedman, New York, NY (US); Joel M. Friedman, South Orange, NJ (US)

(73) Assignees: Albert Einstein College of Medicine, Inc., Bronx, NY (US); La Jolla Bioengineering Institute, La Jolla, CA (US)

( * ) Notice: Subject to any disclaimer, the term of this patent is extended or adjusted under 35 U.S.C. 154(b) by 0 days.

(21) Appl. No.: 14/399,335

(22) PCT Filed: May 1, 2013

(86) PCT No.: PCT/US2013/039051
§ 371 (c)(1),
(2) Date: Nov. 6, 2014

(87) PCT Pub. No.: WO2013/169538
PCT Pub. Date: Nov. 14, 2013

(65) Prior Publication Data
US 2015/0147396 A1   May 28, 2015

Related U.S. Application Data

(60) Provisional application No. 61/643,930, filed on May 8, 2012.

(51) Int. Cl.
*A61K 9/00* (2006.01)
*A61K 31/00* (2006.01)
*A61K 9/51* (2006.01)
*A61K 31/198* (2006.01)
*A61K 31/401* (2006.01)
*A61K 9/14* (2006.01)
*A61K 9/19* (2006.01)
*A61K 31/095* (2006.01)

(52) U.S. Cl.
CPC ............. *A61K 9/51* (2013.01); *A61K 9/141* (2013.01); *A61K 9/146* (2013.01); *A61K 9/19* (2013.01); *A61K 31/095* (2013.01); *A61K 31/198* (2013.01); *A61K 31/401* (2013.01)

(58) Field of Classification Search
CPC .. A61K 31/095; A61K 31/198; A61K 31/401; A61K 9/141; A61K 9/19; A61K 9/51; A61K 9/146
See application file for complete search history.

(56) References Cited

U.S. PATENT DOCUMENTS

| | | | | |
|---|---|---|---|---|
| 2008/0300292 A1* | 12/2008 | Letts | ...................... | A61K 31/04 514/422 |
| 2009/0131342 A1* | 5/2009 | Ellis | ...................... | A61K 31/04 514/29 |
| 2009/0297634 A1* | 12/2009 | Friedman | .............. | A61K 9/0014 424/718 |
| 2011/0049056 A1 | 3/2011 | Wyndham et al. | | |
| 2011/0151000 A1* | 6/2011 | Schultz | ................ | A61K 9/5115 424/484 |
| 2011/0268970 A1* | 11/2011 | Ying | ...................... | B82Y 30/00 428/402 |
| 2013/0344334 A1* | 12/2013 | Schoenfisch | .......... | C07F 7/0874 428/402 |

FOREIGN PATENT DOCUMENTS

CN     101678093 A     3/2010

OTHER PUBLICATIONS

Friedman et al. Sustained release nitric oxide releasing nanoparticles: Characterization of a novel delivery platform based on nitrite containing hydrogel/glass composites. Nitric Oxide 2008, 19:12-20.*
Seabra et al. S-Nitroglutathione incorporated in poly (ethylene glycol) matrix: potential use for topical nitric oxide delivery. Nitric Oxide 11 (2004) 263-272.*
Friedman et al. Improved antimicrobial efficacy with nitric oxide releasing nanoparticle generated S-nitrosoglutathione, Nitric Oxide, Sep. 16, 2011, vol. 25, pp. 381-386.
A.R. Butler, F.W. Flitney, and D.L. Williams, NO, nitrosonium ions, nitroxide ions, nitrosothiols and iron-nitrosyls in biology: a chemist's perspective. Trends Pharmacol Sci 16 (1995) 18-22.
K.A. Hanafy, J.S. Krumenacker, and F. Murad, NO, nitrotyrosine, and cyclic GMP in signal transduction. Med Sci Monit 7 (2001) 801-19.
L.J. McDonald, and F. Murad, Nitric oxide and cyclic GMP signaling. Proc Soc Exp Biol Med 211 (1996) 1-6.
M.W. Radomski, R.M. Palmer, and S. Moncada, Comparative pharmacology of endothelium-derived relaxing factor, nitric oxide and prostacyclin in platelets. Br J Pharmacol 92 (1987) 181-7.

(Continued)

*Primary Examiner* — Robert A Wax
*Assistant Examiner* — Olga V Tcherkasskaya
(74) *Attorney, Agent, or Firm* — Amster, Rothstein & Ebenstein LLP

(57) ABSTRACT

Nanoparticles are provided that comprise S-nitrosothiol (SNO) groups covalently bonded to the nanoparticles and/or S-nitrosothiol containing molecules encapsulated within the nanoparticles, as well as methods of making and using the nanoparticles. The invention also provides methods of preparing nanoparticles comprising Snitrosothiol (SNO) groups covalently bonded to the nanoparticles, where the methods comprise a) providing a buffer solution comprising chitosan, polyethylene glycol, nitrite, glucose, and hydrolyzed 3-mercaptopropyltrimethoxysilane (MPTS); b) adding hydrolyzed tetramethoxysilane (TMOS) to the buffer solution to produce a sol-gel; and c) lyophilizing and ball milling the sol-gel to produce nanoparticles of a desired size.

8 Claims, 11 Drawing Sheets

(56) References Cited

OTHER PUBLICATIONS

M.A. Marietta, P.S. Yoon, R. Iyengar, C.D. Leaf, and J.S. Wishnok, Macrophage oxidation of L-arginine to nitrite and nitrate: nitric oxide is an intermediate. Biochemistry 27 (1988) 8706-11.
J.B. Hibbs, Jr., R.R. Taintor, Z. Vavrin, and E.M. Rachlin, Nitric oxide: a cytotoxic activated macrophage effector molecule. Biochem Biophys Res Commun 157 (1988) 87-94.
D.J. Stuehr, S.S. Gross, I. Sakuma, R. Levi, and C.F. Nathan, Activated murine macrophages secrete a metabolite of arginine with the bioactivity of endothelium derived relaxing factor and the chemical reactivity of nitric oxide. J Exp Med 169 (1989) 1011-20.
C.P. de Oliveira, F.I. Simplicio, V.M. de Lima, K. Yuahasi, F.P. Lopasso, V.A. Alves, D.S. Abdalla, F.J. Carrilho, F.R. Laurindo, and M.G. de Oliveira, Oral administration of S-nitroso-N-acetylcysteine prevents the onset of non alcoholic fatty liver disease in rats. World J Gastroenterol 12 (2006) 1905-11.
H. Rubbo, V. Darley-Usmar, and B.A. Freeman, Nitric oxide regulation of tissue free radical injury. Chem Res Toxicol 9 (1996) 809-20.
S.R. Jaffrey, and S.H. Snyder, Nitric oxide: a neural messenger. Annu Rev Cell Dev Biol 11 (1995) 417-40.
A. Friedman, and J. Friedman, New biomaterials for the sustained release of nitric oxide: past, present, and future. Expert Opinion on Drug Delivery 6 (2009) 1113-1122.
G.R. Thatcher, An introduction to NO-related therapeutic agents. Curr Top Med Chem 5 (2005) 597-601.
P.J. Henry, O.H. Drummer, and J.D. Horowitz, S-nitrosothiols as vasodilators: implications regarding tolerance to nitric oxide-containing vasodilators. Br J Pharmacol 98 (1989) 757-66.
E.A. Kowaluk, R. Poliszczuk, and H.L. Fung, Tolerance to relaxation in rat aorta: comparison of an S-nitrosothiol with nitroglycerin. Eur J Pharmacol 144 (1987) 379-83.
K.F. Ricardo, S.M. Shishido, M.G. de Oliveira, and M.H. Krieger, Characterization of the hypotensive effect of S-nitroso-N-acetylcysteine in normotensive and hypertensive conscious rats. Nitric Oxide 7 (2002) 57-66.
J.N. Bates, M.T. Baker, R. Guerra, Jr., and D.G. Harrison, Nitric oxide generation from nitroprusside by vascular tissue. Evidence that reduction of the nitroprusside anion and cyanide loss are required. Biochem Pharmacol 42 Suppl (1991) S157-65.
A.R. Butler, C. Glidewell, J. McGinnis, and W.I. Bisset, Further investigations regarding the toxicity of sodium nitroprusside. Clin Chem 33 (1987) 490-2.
G. Hagan, and J. Pepke-Zaba, Pulmonary hypertension, nitric oxide and nitric oxide-releasing compounds. Expert Rev Respir Med 5 163-71.
A.R. Butler, and P. Rhodes, Chemistry, analysis, and biological roles of S-nitrosothiols. Anal Biochem 249 (1997) 1-9.
C.F. Lam, S. Sviri, K.F. Ilett, and P.V. van Heerden, Inhaled diazeniumdiolates (NON Oates) as selective pulmonary vasodilators. Expert Opin Investig Drugs 11 (2002) 897-909.
C.M. Maragos, D. Morley, D.A. Wink, T.M. Dunams, J.E. Saavedra, A. Hoffman, A.A. Bove, L. Isaac, J.A. Hrabie, and L.K. Keefer, Complexes of .NO with nucleophiles as agents for the controlled biological release of nitric oxide. Vasorelaxant effects. J Med Chem 34 (1991) 3242-7.
C.M. Maragos, J.M. Wang, I.A. Hrabie, J.J. Oppenheim, and L.K. Keefer, Nitric oxide/nucleophile complexes inhibit the in vitro proliferation fo A375 melanoma cells via nitric oxide release. Cancer Res 53 (1993) 564-8.
A.J. Friedman, G. Han, M.S. Navati, M. Chacko, L. Gunther, A. Alfieri, and J.M. Friedman, Sustained release nitric oxide releasing nanoparticles: characterization of a novel delivery platform based on nitrite containing hydrogel/glass composites. Nitric Oxide 19 (2008) 12-20.
G. Han, A.J. Friedman, and J.M. Friedman, Nitric oxide releasing nanoparticle synthesis and characterization. Methods Mol Biol 704 (2011) 187-95.
P. Cabrales, G. Han, C. Roche, P. Nacharaju, A.I. Friedman, and J.M. Friedman, Sustained release nitric oxide from long-lived circulating nanoparticles. Free Radic Biol Med 49 (2010) 530-8.
P. Cabrales, G. Han, P. Nacharaju, A.I. Friedman, and J.M. Friedman, Reversal of hemoglobin-induced vasoconstriction with sustained release of nitric oxide. Am J Physiol Heart Circ Physiol 300 (2011) H49-56.
G. Han, M. Tar, D.S. Kuppam, A. Friedman, A. Melman, J. Friedman, and K.P. Davies, N anoparticles as a novel delivery vehicle for therapeutics targeting erectile dysfunction. J Sex Med 7 (2010) 224-33.
A Friedman, K. Blecher. D. Sanchez, C. Tuckman-Vernon, P. Gialanella, J.M. Friedman, L.R. Martinez, and J.D. Nonsanchuk, Susceptibility of Gram-positive and- negative bacteria to novel nitric oxide-releasing nanoparticle technology. Virulence 2 (2011) 217-21.
A.J. Friedman, K. Blecher, D. Schairer, C. Tuckman-Vernon, P. Nacharaju, D. Sanchez, P. Gialanella, L.R. Martinez, J.M. Friedman, and J.D. Nosanchuk, Improved antimicrobial efficacy with nitric oxide releasing nanoparticle generated Snitrosoglutathione. Nitric Oxide 25 (2011) 3 81-6.
G. Han, L.R. Martinez, M.R. Mihu, A.J. Friedman, J.M. Friedman, and J.D. Nosanchuk, Nitric oxide releasing nanoparticles are therapeutic for *Staphylococcus aureus* abscesses in a murine model of infection. PLoS One 4 (2009) e7804.
M.R. Mihu, U. Sandkovsky, G. Han, J.M. Friedman, J.D. Nosanchuk, and L.R. Martinez, The use of nitric oxide releasing nanoparticles as a treatment against Acinetobacter baumannii in wound infections. Virulence 1(2010)62-7.
L.R. Martinez, G. Han, M. Chacko, M.R. Mihu, M. Jacobson, P. Gialanella, A.J. Friedman, J.D. Nosanchuk, and J.M. Friedman, Antimicrobial and healing efficacy of sustained release nitric oxide nanoparticles against *Staphylococcus aureus* skin infection. J Invest Dermatol 129 (2009) 2463-9.
H.H. Al-Sa'doni, and A. Ferro, S-nitroxothiols as nitric oxide-donors: chemistry, biology and possible future therapeutic applications. Curr Med Chem 11 (2004) 2679-90.
D.L. Diesen, D.T. Hess, and J.S. Stamler, Hypoxic vasodilation by red blood cells: evidence for an s-nitrosothiol-based signal. Circ Res 103 (2008) 545-53.
M.W. Foster, D.T. Hess, and J.S. Stamler, Protein S-nitrosylation in health and disease: a current perspective. Trends Mol Med 15 (2009) 391-404.
M.W. Foster, T.J. McMahon, and J.S. Stamler, S-nitrosylation in health and disease. Trends Mol Med 9 (2003) 160-8.
D.Giustarini, A. Milzani, R. Colombo, I. Dalle-Donne, and R. Rossi, Nitric oxide and S-nitrosothiols in human blood. Clin Chim Acta 330 (2003) 85-98.
J.S. Stamler, D.I. Simon, I.A. Osborne, M.E. Mullins, 0. Jaraki, T. Michel, D.J. Singel, and J. Loscalzo, S-nitrosylation of proteins with nitric oxide: synthesis and characterization of biologically active compounds. Proc Natl Acad Sci U S A 89 (1992) 444-8.
T.M. Hu, and T.C. Chou, The kinetics of thiol-mediated decomposition of S-nitrosothiols. Aaps J 8 (2006) E485-92.
L. Grossi, and P.C. Montevecchi, A kinetic study of S-nitrosothiol decomposition. Chemistry 8 (2002) 380-7.
G. Richardson, and N. Benjamin, Potential therapeutic uses for S-nitrosothiols. Clin Sci (Lond) 102 (2002) 99-105.
B.T. Mellion, L.J. Ignarro, C.B. Myers, E.H. Ohlstein, B.A. Ballot, A.L. Hyman, and P.J. Kadowitz, Inhibition of human platelet aggregation by S-nitrosothiols. Hemedependent activation of soluble guanylate of cyclic GMP accumulation. Mol Pharmacol 23 (1983) 653-64.
H. Al-Sa'doni, and A. Ferro, S-Nitrosothiols: a class of nitric oxide-donors drugs. Clin Sci (Lond) 98 (2000) 507-20.
H.H. Al-Sa'doni, I.Y. Khan, L. Poston, I. Fisher, and A. Ferro, A novel family of S-nitrosothiols: chemical synthesis and biological actions. Nitric Oxide 4 (2000) 550-60.
L.J. Ignarro, H. Lippton, J.C. Edwards, W.H. Baricos, A.L. Hyman, P.J. Kadowitz, and C.A. Gruetter, Mechanism of vascular smooth muscle relaxation by organic nitrates, nitrites, nitroprusside and nitric oxide: evidence for the involvement of S-nitrosothiols as active intermediates. J Pharmacol Exp Ther 218 (1981) 739-49.

(56) References Cited

OTHER PUBLICATIONS

M.H. Krieger, K.F. Santos, S.M. Shishido, A.C. Wanschel, H.F. Estrela, L. Santos, M.G. De Oliveira, K.G. Franchini, R.C. Sparadi-Bratfisch, and F.R. Laurindo, Antiatherogenic effects of S-nitroso-N-acetylcysteine in hypercholesterolemic LDL receptor knockout mice. Nitric Oxide 14 (2006) 12-20.

J.A. Garcia, L. dos Santos, A.L. Moura, K.F. Ricardo, A.C. Wanschel, S.M. Shishido, R.C. Spadari-Bratfisch, H.P. de Souza, and M.H. Krieger, S-nitroso-N-acetylcysteine (SNAC) prevents myocardial alterations in hypercholesterolemic LDL receptor knockout mice by antiinflammatory action. J Cardiovasc Pharmacol 51 (2008) 78-85.

P. Nachuraju, A.I. Friedman, J.M. Friedman, and P. Cabrales, Exogenous nitric oxide prevents cardiovascular collapse during hemorrhagic shock. Resuscitation 82 (2011) 607-13.

A. Colantuoni, S. Bertuglia, and M. Intaglietta, Quantitation of rhythmic diameter changes in arterial microcirculation. Am J Physiol 246 (1984) H508-H517.

M. Sokoto, A. Yoshida, and M. Haga, Methemoglobin in blood as determined by double-wavelength spectrophotometry. Clin Chem 28 (1982) 508-11.

A.J. Friedman, G. Han, M.S. Navati, M. Chacko, L. Gunther, A. Alfieri, and J.M. Friedman, Sustained release nitric oxide releasing nanoparticles: Characterization of a novel delivery platform based on nitrite containing hydrogel/glass composites. Nitric Oxide-Biology and Chemistry 19 (2008) 12-20.

F. Murad, Cyclic guanosine monophosphate as a mediator of vasodilation. J Clin Invest 78 (1986) 1-5.

B. Lima, M.T. Forrester, D.T. Hess, and J.S. Stamler, S-nitrosylation in cardiovascular signaling. Circ Res 106 (2010) 633-46.

J.C. Wanstall, K.L. Homer, and S.A. Doggrell, Evidence for, and importance of, cGMP-independent mechanisms with NO and NO donors on blood vessels and platelets. Curr Vasc Pharmacol 3 (2005) 41-53.

A.M. Hamad, A. Clayton, B. Islam, and A.I. Knox, Guanylyl cyclases, nitric oxide, natriuretic peptides, and airway smooth muscle function. Am J Physiol Lung Cell Mol Physiol 285 (2003) L973-83.

G.P. Ahern, V.A. Klyachko, and M.B. Jackson, cGMP and S-nitrosylation: two routes for modulation of neuronal excitability by NO. Trends Neurosci 25 (2002) 510-7.

B. Brune, S. Mohr, and U.K. Messmer, Protein thiol modification and apoptotic cell death as cGMP-independent nitric oxide (NO) signaling pathways. Rev Physiol Biochem Pharmacol 127 (1996) 1-30.

F. Murad, Nitric oxide and cyclic guanosine monophosphate signaling in the eye. Can J Ophthalmol 43 (2008) 291-4.

G. Boerrigter, H. Lapp, and J.C. Burnett, Modulation of cGMP in heart failure: a new therapeutic paradigm. Handb Exp Pharmacol (2009) 485-506.

N. Hogg, The biochemistry and physiology of S-nitrosothiols. Annu Rev Pharmacol Toxicol 42 (2002) 585-600.

M.P. Gordge, J.S. Hothersall, and A.A. Noronha-Dutra, Evidence for a cyclic GMP-independent mechanism in the anti-platelet action of S-nitrosoglutathione. Br J Pharmacol 124 (1998) 141-8.

LS. Severina, O.G. Bussygina, N.V. Pyatakova, LV. Malenkova, and A.F. Vanin, Activation of soluble guanylate cyclase by NO donors—S-nitrosothiols, and dinitrosyliron complexes with thiol-containing ligands. Nitric Oxide 8 (2003) 155-63.

A.R. Butler, H.H. Al-Sa'doni, LL. Megson, and F.W. Flitney, Synthesis, decomposition, and vasodilator action of some new S-nitrosated dipeptides. Nitric Oxide 2 (1998) 193-202.

E.A. Kowaluk, and H.L. Fung, Spontaneous liberation of nitric oxide cannot account for in vitro vascular relaxation by S-nitrosothiols. J Pharmacol Exp Ther 255 (1990) 1256-64.

W.R. Mathews, and S.W. Kerr, Biological activity of S-nitrosothiols: the role of nitric oxide. J Pharmacol Exp Ther 267 (1993) 1529-37.

V.S. Fernandes, A. Martinez-Saenz, P. Recio, A.S. Ribeiro, A. Sanchez, M.P. Martinez, A.C. Martinez, A. Garcia-Sacristan, L.M. Orensanz, D. Prieto, and M. Hernandez, Mechanisms involved in the nitric oxide induced vasorelaxation in porcine prostatic small arteries. Naunyn Schmiedebergs Arch Pharmacol 3 84 (2011) 245-53.

R. Priora, A. Margaritis, S. Frosali, L. Coppo, D. Summa, D. Di Giuseppe, C. Aldinucci, G. Pessina, A. Di Stefano, and P. Di Simplicio, In vitro inhibition of human and rat platelets by NO donors, nitrosoglutathione, sodium nitroprusside, and SIN-I, through activation of cGMP-independent pathways. Pharmacol Res 64 (2011) 289-97.

J.S. Stamler, S-nitrosothiols and the bioregulatory actions of nitrogen oxides through reactions with thiol groups. Curr Top Microbiol Immunol 196 (1995) 19-36.

D.R. Arnelle, and J.S. Stamler, NO+, NO, and NO− donation by S-nitrosothiols: implications for regulation of physiological functions by S-nitrosylation and acceleration of disulfide formation. Arch Biochem Biophys 318 (1995) 279-85.

D.T. Hess, A. Matsumoto, S.O. Kim, H.E. Marshall, and J.S. Stamler, Protein S-nitrosylation: purview and parameters. Nat Rev Mol Cell Biol 6 (2005) 150-66.

J.L. Alencar, L Lobysheva, K. Chalupsky, M. Geffard, F. Nepveu, J.C. Stoclet, and B. Muller, S-nitrosating nitric oxide donors induce long-lasting inhibition of contraction in isolated arteries. J Pharmacol Exp Ther 307 (2003) 152-9.

A. Slivka, R. Chuttani, D.L. Carr-Locke, L. Kobzik, D.S. Bredt, J. Loscalzo, and J.S. Stamler, Inhibition of spincter of Oddi function by the nitric oxide carrier S-nitroso-N-acetylcysteine in rabbits and humans. J Clin Invest 94 (1994) 1792-8.

A.J. de Belder, R. MacAllister, M.W. Radomski, S. Moncada, and P.J. Vallance, Effects of S-nitroso-glutathione in the human forearm circulation: evidence for selective inhibition of platelet activation. Cardiovasc Res 28 (1994) 691-4.

B. Ramsay, M. Radomski, A. De Belder, J.F. Martin, and P. Lopez-Jaramillo, Systemic effects of S-nitroso-glutathione in the human following intravenous infusion. Br J Clin Pharmacol 40 (1995) 101-2.

E.J. Langford, A.S. Brown, R.J. Wainwright, A.I. de Belder, M.R. Thomas, R.E. Smith, M.W. Radomski, J.F. Martin, and S. Moncada, Inhibition of platelet activity by S-nitrosoglutathione during coronary angioplasty. Lancet 344 (1994) 1458-60.

C. Lees, E. Langford, A.S. Brown, A. de Belder, A. Pickles, J.F. Martin, and S. Campbell, The effects of S-nitrosoglutathione on platelet activation, hypertension, and uterine and fetal Doppler in sever preeclampsia. Obstet Gynecol 88 (1996) 14-9.

U. Elkayam, M. Janmohamed, M. Habib, and P. Hatamizadeh, Vasodilators in the management of acute heart failure. Crit Care Med 36 (2008) S95-105.

J.D. Kirk, J.T. Parissis, and G. Filippatos, Pharmacologic stabilization and management of acute heart failure syndromes in the emergency department. Heart Fail Clin 5 (2009) 43-54, vi.

J.W. Park, Dual role of S-nitrosocaptopril as an inhibitor of angiotensin-converting enzyme and a nitroso group carrier. Biochem Biophys Res Commun 189 (1992) 206-10.

T.P. Dasgupta, and D.V. Aquart, Transfer of nitric oxide from nitrovasodilators to free thiols—evidence of two distinct stages. Biochem Biophys Res Commun 335 (2005) 730-3.

L. Jia, and R.C. Blantz, The effects of S-nitrosocaptopril on renal filtration and blood pressure in rats. Eur J Pharmacol 354 (1998) 33-41.

D.Y. Tsui, A. Gambino, and J.C. Wanstall, S-nitrosocaptopril: acute in-vivo pulmonary vasodepressor effects in pulmonary hypertensive rats. J Pharm Pharmacol 55 (2003) 1121-5.

International Search Report dated Sep. 13, 2013 for the corresponding PCT Application No. PCT/US2013/039051.

D. Schairer, L. Martinez, K. Blecher, J. Chouake, P. Nacharju, P. Gialanella, J.M. Friedman, J. Nosanchuk, and A. Friedman, Nitric oxide nanoparticles: Pre-clinical utility as a therapeutic for intramuscular abscesses. Virulence 3 (2012), vol. 3:1, pp. 62-67.

I. Homyak, K. Marosi, L. Kiss, P. Grof, and Z. Lacza, Increased stability of S-nitrosothiol solutions via pH modulations. Free Radic Research, Feb. 2012; vol. 46(2); pp. 214-225.

(56) References Cited

OTHER PUBLICATIONS

International Search Report and Written Opinion dated Sep. 13, 2013 for the corresponding PCT Application No. PCT/US2013/039051.

International Preliminary Report on Patentability in corresponding PCT Application No. PCT/US2013/039051, dated Nov. 11, 2014.

\* cited by examiner

A

B

C

NANOPARTICLE DELIVERY VEHICLE FOR S-NITROSO-N-ACETYL CYSTEINE AND USES THEREOF

CROSS-REFERENCE TO RELATED APPLICATION

This application is a U.S. National Phase Application under 35 U.S.C. § 371 of International Patent Application No. PCT/US2013/039051, May 1, 2013, and claims the benefit of priority under 35 U.S.C. Section 119(e) of U.S. Application Ser. No. 61/643,930, filed May 8, 2012, all of which are incorporated by reference in their entireties. The International Application was published on Nov. 14, 2013 as International Publication No, WO 2013/169538 A1.

BACKGROUND OF THE INVENTION

Throughout this application various publications are referred to in brackets. Full citations for these references may be found at the end of the specification immediately preceding the claims. The disclosures of these publications more fully describe the art to which the subject application pertains.

Nitric oxide (NO) is a small, diatomic gaseous molecule with numerous biological functions. Most notably, it is the major endothelial relaxing factor that relaxes smooth muscle by activating guanylate cyclase, which, downstream, results in vasodilation via a cyclic guanosine monophosphate-dependent pathway [1; 2; 3]. NO has many other functions that highlight its biomedical importance and therapeutic potential. NO inhibits platelet aggregation [1; 4], plays a major role in macrophage-mediated inflammatory response [1; 5; 6; 7], has antioxidant properties that prevent lipid peroxidation [8; 9], and can function as a signaling molecule in several tissue types including neurons and fibroblasts [1; 10]. The particular physiological consequence of NO is dependent not only on the site/compartment of production but also on both the rate and amount of NO generated at that location. Despite the many potential therapeutic benefits of supplemental NO, its use as a therapeutic has been limited. This limitation is due in part to the ongoing challenge of creating a practical and economically feasible delivery vehicle for this moderately reactive molecule that is capable of sustained delivery of the appropriate amount of NO to a desired target site [11].

Over the past few decades, several NO-related therapeutics have emerged, though are generally based on complex chemical systems. Unfortunately, these chemical reagents typically cannot spontaneously release NO. Instead, they rely on enzymatic activity to achieve release of NO [12]. These so-called pro-drugs include organonitrates, most notably nitroglycerine and organometallic NO-donors such as sodium nitroprusside. Disadvantages including progressive tachyphylaxis, resulting from depletion of host enzymes required for the generation of NO, potential toxicity from toxic byproducts (e.g., sodium nitroprusside decomposes releasing NO as well as cyanide) [13; 14; 15; 16; 17], and short lived biological impact, all limit their therapeutic efficacy. Gaseous NO, though effective and approved by the FDA for the treatment of pulmonary hypertension [18], is limited due to expense, requirement of delivery via gas tank, and potential toxicity issues from the production of $NO_2$ [19]. Diazeniumdiolates (commonly referred to as NONOates) are a new class of chemicals which can release NO spontaneously. NONOates contain NO complexed with nucleophiles [20; 21; 22], allowing for controllable rates of NO release via various parameters including pH, temperature and the nature of the nucleophile with which the NO is complexed. Unfortunately, pulmonary and systemic toxicity induced by metabolites of NONOates are a potential issue, as is the formation of met hemoglobin (metHb) limiting red blood cell (RBC) oxygen carrying capacity [20].

Recently, novel hydrogel-based nanoparticle platforms have been described capable of releasing internally generated NO at biologically significant levels over sustained time periods [23; 24]. Upon IV infusion, these NO releasing nanoparticles (NO-nps) have been shown to induce long-lived vasodilatory effects in animal models in a dose-dependent manner with much greater efficacy and less metHb build up than NONOates [25]. These infused NO-nps have also been shown to be effective in reversing acellular Hb induced vasoconstriction and in limiting the inflammatory cascade in a hemorrhagic shock model [26]. Topical NO-nps have been effective in treating erectile dysfunction in rat models [27], have potent broad spectrum anti-microbial activity [28; 29] in vitro, and accelerate wound and abscess healing in murine models [30; 31; 32; 33].

S-nitrosothiols containing molecules (RSNOs) have come into the biotechnology spotlight recently as molecules that once formed, can extend both the temporal window and functionality for NO associated bioactivity in vivo [34; 35; 36; 37; 38; 39]. RSNO half-lives are measured in the minutes to hours [40; 41; 42], whereas free NO has been shown to have a half-life measured in the seconds or less depending on site of production [1]. RSNO-based therapeutics appear to have many very similar physiologic effects as other NO-related therapeutics [34; 43; 44; 45]. They are long-lasting bioactive vasodilators [13; 15; 19; 44] not subject to drug tolerance [13; 14; 15; 19; 46], relax smooth muscle [47], and prevent platelet aggregation [43]. In animal models NAC-SNO reduces plaque buildup secondary to hypercholesterolemia [48], acts as a hypotensive [15], an anti-inflammatory [49], and blocks lipid peroxidation that can limit non-alcoholic fatty liver disease pathology [8]. Much of the biological activity of RSNOs has been attributed to S-transnitrosation, where NO as a nitroso group is transferred from one thiol to another resulting in the nitrosation of reactive thiol containing proteins on cell surfaces, in cells, and in plasma.

The present invention addresses the need for a practical and economically feasible delivery vehicle that is capable of sustained delivery of NO to a desired target site.

SUMMARY OF THE INVENTION

The invention is directed to nanoparticles comprising S-nitrosothiol (SNO) groups covalently bonded to the nanoparticles and/or S-nitrosothiol containing molecules encapsulated within the nanoparticles.

The invention also provides methods of preparing nanoparticles comprising S-nitrosothiol (SNO) groups covalently bonded to the nanoparticles, where the methods comprise a) providing a buffer solution comprising chitosan, polyethylene glycol, nitrite, glucose, and hydrolyzed 3-mercaptopropyltrimethoxysilane (MPTS); b) adding hydrolyzed tetramethoxysilane (TMOS) to the buffer solution to produce a sol-gel; and c) lyophilizing and ball milling the sol-gel to produce nanoparticles of a desired size.

The invention further provides methods of preparing nanoparticles comprising a S-nitrosothiol containing molecule encapsulated within the nanoparticle, where the methods comprise a) providing a buffer solution comprising chitosan, polyethylene glycol, nitrite, glucose, and a S-nitrosothiol containing molecule; b) adding hydrolyzed tetramethoxysilane (TMOS) to the buffer solution to produce a sol-gel; and c) lyophilizing and ball milling the sol-gel to produce nanoparticles of a desired size.

DETAILED DESCRIPTION OF THE INVENTION

Figures 1A, 1B:
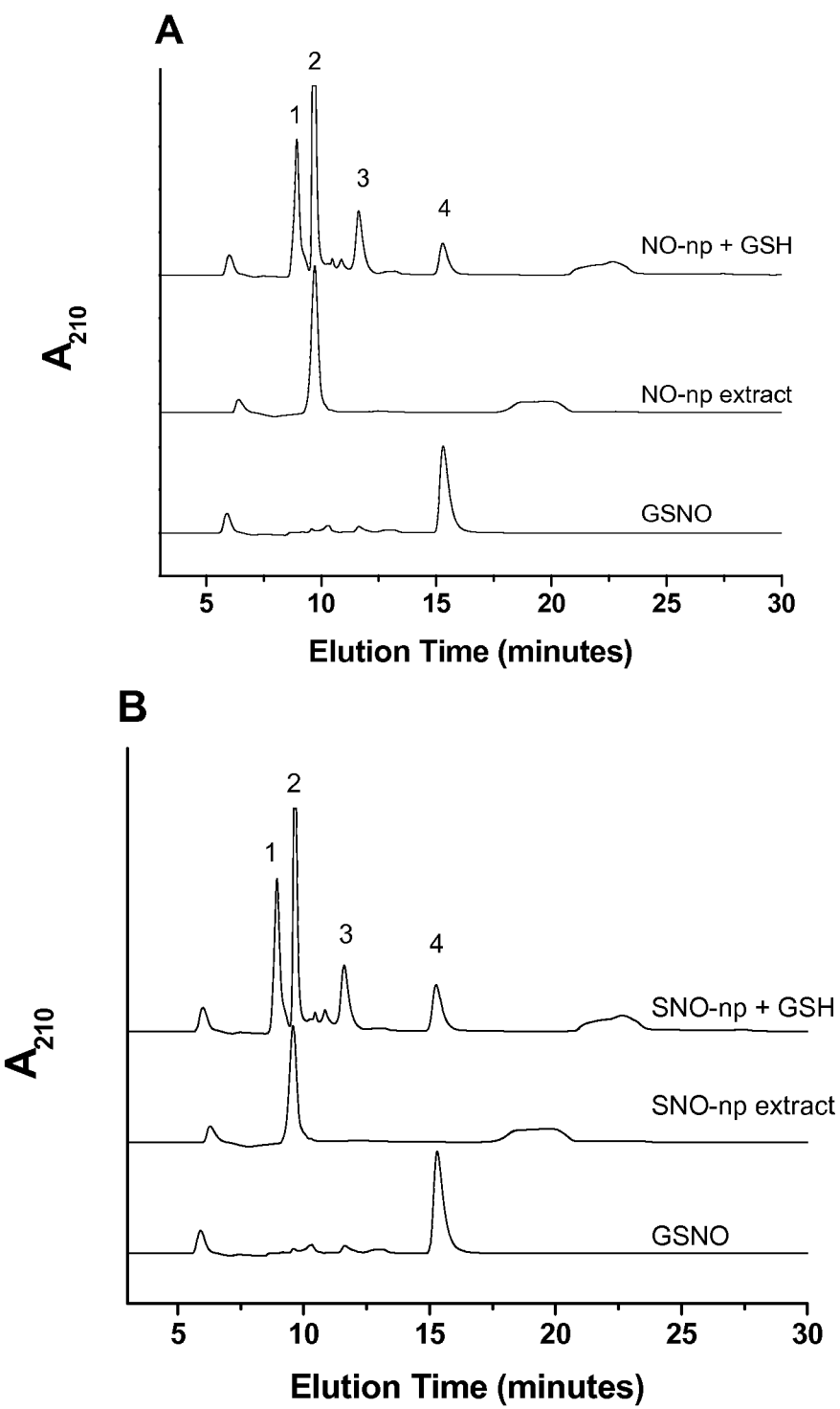
FIG. 1A-1C. GSNO production from nanoparticles. NO-np (A), SNO-np (B), and NAC-SNO-np-2 (C) were incubated at 20 mg/ml in 0.5 mM DTPA/PBS, pH 7.4 for 1 hour at room temperature shielded from light in the absence and presence of GSH (20 mM) while mixing on a lab rotator. Supernatants were diluted (100× for extracts and 50× for GSH-reaction mixtures) and analyzed by RPHPLC as described in the text. GSH-reaction mixtures of all the particles displayed a peak corresponding to GSNO, which was absent in the respective extracts (in the absence of GSH). Peaks identities are as follows: 1=GSH, 2=nitrite, 3=GSSG, 3a=nitrate, 4=GSNO, 5=non-characterized oxidized product of NAC-SNO, 6=NAC-SNO.

The invention is directed to a nanoparticle comprising S-nitrosothiol (SNO) groups covalently bonded to the nanoparticle and/or a S-nitrosothiol containing molecule encapsulated within the nanoparticle.

Examples of S-nitrosothiol containing molecules that can be encapsulated within the nanoparticle include, but are not limited to, S-nitroso-N-acetyl cysteine (NAC-SNO) and/or S-nitroso-captopril (captopril-SNO).

The nanoparticles can comprise, for example, silica, chitosan, polyethylene glycol, nitrite, glucose, hydrolyzed tetramethoxysilane (TMOS) and hydrolyzed 3-mercaptopropyltrimethoxysilane (MPTS). The nanoparticles can also comprise, for example, silica, chitosan, polyethylene glycol, nitrite, glucose, hydrolyzed tetramethoxysilane (TMOS), and N-acetyl-L-cysteine and/or S-nitroso-captopril. Preferably, the nanoparticles comprise nitrite and thiol in a concentration ratio of 1:0.625 to 1:2.5.

The nanoparticles can have a diameter of 10 nm to 100 μm, preferably 10 nm to 10 μm, and more preferably 10 nm to 1 μm. Preferably, the nanoparticles have an average diameter of less than about 500 nm, more preferably less than about 250 nm, and most preferably less than about 150 nm.

Preferably, the polyethylene glycol (PEG) has a molecular weight of 200 to 20,000 Daltons and more preferably 400 to 10,000 Daltons. A preferred polyethylene glycol has a molecular weight of 400 Daltons. In another embodiment, the PEG is PEG 5,000 to PEG 10,000. PEGs of various molecular weights, conjugated to various groups, can be obtained commercially, for example from Nektar Therapeutics, Huntsville, Ala.

The invention also provides a method of preparing nanoparticles comprising S-nitrosothiol (SNO) groups covalently bonded to the nanoparticles, the method comprising:

a) providing a buffer solution comprising chitosan, polyethylene glycol, nitrite, glucose, and hydrolyzed 3-mercaptopropyltrimethoxysilane (MPTS);

b) adding hydrolyzed tetramethoxysilane (TMOS) to the buffer solution to produce a sol-gel; and c) lyophilizing and ball milling the sol-gel to produce nanoparticles of a desired size.

The invention further provides a method of preparing nanoparticles comprising a S-nitrosothiol containing molecule encapsulated within the nanoparticle, the method comprising:

a) providing a buffer solution comprising chitosan, polyethylene glycol, nitrite, glucose, and a S-nitrosothiol containing molecule;

b) adding hydrolyzed tetramethoxysilane (TMOS) to the buffer solution to produce a sol-gel; and c) lyophilizing and ball milling the sol-gel to produce nanoparticles of a desired size.

Preferably MPTS is hydrolyzed with HCl by sonication on an ice-bath. Preferably, TMOS is hydrolyzed with HCl by sonication on an ice-bath.

The S-nitrosothiol containing molecule encapsulated within the nanoparticle can be, for example, S-nitroso-N-acetyl cysteine (NAC-SNO) and/or S-nitroso-captopril (captopril-SNO).

The nanoparticles formed by the methods disclosed herein can have a diameter of, for example, 10 nm to 100 µm.

The invention further provides a nanoparticle produced by any of the methods disclosed herein.

The invention further provides a pharmaceutical composition comprising any of the nanoparticles disclosed herein and a pharmaceutically acceptable carrier.

The nanoparticles disclosed herein or the pharmaceutical compositions disclosed herein provide sustained release of nitric oxide (NO) that is more sustained than release of NO from a NO-containing nanoparticle that does not contain S-nitrosothiol (SNO) groups covalently bonded to the nanoparticle and/or S-nitroso-N-acetyl cysteine (NAC-SNO) encapsulated within the nanoparticle.

The nanoparticles described herein can be delivered to a subject by a variety of topical or systemic routes of delivery, including but not limited to percutaneous, inhalation, oral, local injection and intravenous introduction. The nanoparticles can be incorporated, for example, in a cream, ointment, transdermal patch, implantable biomedical device or scrub.

The invention also provides a method of treating an infection in a subject comprising administering to the subject any of the nanoparticles disclosed herein in an amount and manner effective to treat the infection. The nanoparticles can be administered topically or systemically depending on the site of the infection.

The term "infection" is used to include infections that produce an infectious disease. The infection diseases include communicable diseases and contagious diseases. As used herein, the term "treat" an infection means to eliminate the infection, to reduce the size of the infection, to prevent the infection from spreading in the subject, or to reduce the further spread of the infection in the subject.

The infection can be, for example, a bacterial, viral, fungal or parasitic infection. The bacterial infection can be a Staphylococcal infection. The bacterial infection can be caused, for example, by a bacterium selected from the group consisting of *S. aureus*, Multidrug-resistant or Methicillin-resistant *S. aureus* (MRSA), *P. aeruginosa*, *B. circulans*, *B. cereus*, *E. coli*, *P. vulgaris*, *P. acnes*, *S. pyognenes*, *S. enterica*, *V. anguillarum*, *K pneumoniae*, *P. piscicida*, *P. aeruginosa*, *A. tumefaciens*, *C. micgiganence*, *A. mali*, *E. chrysanthemi*, *X campestris*, *C. diplodiella*, *P. piricola*, *M. tuberculosis*, and *M. ulcerans*. The fungal infection can be caused, for example, by a fungus selected from the group consisting of *T. equinum*, *C. Albicans*, *F. oxysporum*, *R. solani*, *B. cinerea*, and *A. flavus*. The viral infection can be caused, for example, by a virus selected from the group consisting of *M. contagiosum*, *Rota*, *Papilloma*, *Parvo*, and *Varicella*. The parasite infection can be caused, for example, by a parasite of the genus *Plasmodium*, *Leishmania*, *Schistosoma*, *Austrobilharzia*, *Heterobilharzia*, *Ornithobilharzia* or *Cryptosporidium*, for example *P. falciparum*.

The invention also provides a method of promoting angiogenesis, vasodilation, smooth muscle relaxation, wound healing, or hair growth in a subject comprising administering to the subject any of the nanoparticles disclosed herein in an amount and manner effective to promote angiogenesis, vasodilation, smooth muscle relaxation, wound healing, or hair growth.

The invention further provides a method of treating a disease or disorder in a subject comprising administering to the subject any of the nanoparticles disclosed herein in an amount and manner effective to treat the disease or disorder, wherein the disease or disorder is treatable with nitric oxide (NO). Diseases or disorders that are treatable with NO include, for example, hypertension, peripheral vascular disease, platelet aggregation, erectile dysfunction, ischemia, inflammation, erectile dysfunction, a wound, an abscess, scleroderma and sickle cell anemia. The term "treat" a disease or disorder means to reduce or eliminate a sign or symptom of the disease or disorder, to stabilize the disease or disorder, or to reduce further progression of the disease ordisorder.

Abbreviations used in this application include: NO, nitric oxide; GSH, glutathione; GSNO, S-nitrosoglutathione; RSNO, S-nitrosothiols containing molecules; NO-np, nitric oxide releasing nanoparticles; SNO-np, S-nitrosothiol loaded nanoparticles; NAC-SNO-np, S-nitroso-N-acetylcysteine releasing nanoparticles; TMOS, Tetramethoxysilane; MPTS, 3-mercaptopropyltrimethoxysilane; RPHPLC, reverse phase high performance liquid chromatography; PBS, phosphate buffered saline; DTPA, diethylenetriamine-penta-acetic acid; MAP, mean arterial blood pressure; HR, heart rate; MetHb, methemoglobin; RBCs, red blood cells; and BE, base excess.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Nitric oxide releasing nanoparticles (NO-np), when combined with glutathione (GSH), effectively and efficiently generate GSNO, which due to its long half-life and ability to transnitrosate, has greater antimicrobial activity then NO-np alone against clinical isolates of gram positive and negative multi drug resistant pathogens [28]. Given both the extended bioactive lifetime of RSNO compared to free NO and the potential differences in target tissues/cells and the success achieved with the NO releasing nanoparticle platform [25; 26; 27; 28; 30; 32; 50], it was undertaken to produce nanoparticles that were similar in character and structure, but with the capability of either releasing RSNO species or transferring NO via S-transnitrosation.

In the current study, two novel S-nitrosothiol containing hydrogel-based nanoparticle platforms are presented and compared to the NO-np. The first platform (SNO-np) is a SNO loaded nanoparticle in which the thiols are covalently integrated into the polymeric network of the hydrogel comprising the nanoparticle. The S-nitrosothiol moiety cannot leak out from these particles, and therefore, as a consequence, the particles can only release NO or transfer NO to an external thiol containing molecule with which the SNO-np makes contact. The second platform (NAC-SNO-np) is a nanoparticle with a population of encapsulated NAC-SNO. In this platform, there is also the potential for S-transnitrosation to an external thiol containing molecule. However, with this platform, NAC-SNO as well as NO and other NAC associated products can be released from the nanoparticle at a slow sustained rate. The efficiency with which each platform generates GSNO was determined, and a comparison was made of the superior platform to the NO-np in its ability to transnitrosate as represented by vasodilation in vivo and by anti-bacterial activity.

Materials and Methods

Materials: TMOS (Tetramethoxysilane), PEG-400, chitosan and all other reagents were purchased from Sigma. MPTS (3-mercaptopropyltrimethoxysilane) was from Gelest Inc.

Synthesis of NO-np/SNO and np/NAC-SNO-np: A TMOS-based sol-gel method was used to prepare all the nanoparticles as described earlier [23]. Briefly, TMOS (3 ml) was hydrolyzed with 1 mM HCl (0.6 ml) by sonication on an ice-bath. The hydrolyzed TMOS (3 ml) was added to a buffer mixture of 1.5 ml of 0.5% chitosan, 1.5 ml of PEG 400 and 24 ml of 50 mM Phosphate, pH 7.4, containing other molecules of interest as shown in Table 1. For NO-np, the cocktail contained nitrite and glucose. For SNO-np, nitrite, glucose and acid-hydrolyzed MPTS were added to the buffer mixture at pH 3. MPTS (2 ml) was hydrolyzed with 1 mM HCl (1 ml) by sonication over ice and 1.5 ml of the hydrolyzed MPTS was used. Hydrolyzed TMOS (3 ml) was then added, which polymerized resulting in a pink, opaque sol-gel. For NAC-SNO-np, N-acetyl-L-cysteine, nitrite and glucose were used at the ratios as shown in Table 1. All the resulting sol-gels were lyophilized and then ball milled in a planetary ball-mill (Fritsch, "Pulverisette 6") into fine powders.

Np extraction: Nanoparticles (20 mg/ml) were suspended in 0.5 mM diethylenetriaminepenta-acetic acid (DTPA) in phosphate buffered solution (PBS, pH 7.4) and incubated for 1 hour at room temperature on a lab rotator, shielded from light. The mixture was spun down in a micro-centrifuge briefly. A small aliquot of the supernatant (10 µl) was removed, diluted 100× and analyzed on RPHPLC as described below.

GSNO production: Nps were suspended in glutathione (GSH) solutions prepared in 0.5 mM DTPA/PBS (pH 7.4) at room temperature while mixing on a Lab Rotator shielded from light. At time intervals, aliquots were taken out, 50× diluted and analyzed by RPHPLC.

RPHPLC analysis of the GSNO formation reaction: The reaction products were analyzed by RPHPLC using a Vydac Protein and Peptide $C_{18}$ analytical column (250 mm×4.6 mm) in an isocratic 10 mM $K_2HPO_4$/10 mM tetrabutylammonium hydrogen sulfate in 5% acetonitrile running buffer (pH 7.0) at a 0.5 ml/min flow rate and were detected by UV absorbance at 210 nm.

Peak identification and concentration calculation: Peak identities were confirmed by co-elution of known standards from Sigma. GSNO concentrations were determined by peak areas from RPHPLC chromatogram using GSNO standard of known concentration.

Vasodilation Experiments

Animal preparation: Investigations were performed in 50-65 g male Golden Syrian Hamsters (Charles River Laboratories, Boston, Mass.) fitted with a dorsal skinfold chamber window. Animal handling and care followed the NIH Guide for the Care and Use of Laboratory Animals. All experimental protocols were approved by the local animal care committee. The hamster chamber window model is widely used for microvascular studies in the unanesthetized state, and the complete surgical technique is described in detail elsewhere [51].

Inclusion criteria: Animals were suitable for the experiments if: (1) systemic parameters were within normal range, namely, heart rate (HR) 340 beat/min, mean arterial blood pressure (MAP) 80 mm Hg, systemic Hct 45%, and arterial oxygen partial pressure ($P_aO_2$) 50 mm Hg; and (2) microscopic examination of the tissue in the chamber observed under 650× magnification did not reveal signs of edema or bleeding.

Nanoparticle infusion and monitoring systemic parameters: Animals were infused with nanoparticles suspended in deoxygenated saline. Solutions were infused in a volume of 50 µl (equivalent to less than 2% of the animals blood volume) via the jugular vein at a rate of 100 µl/min. MAP and HR were recorded continuously (MP 150, Biopac System; Santa Barbara, Calif.). Hct was measured from centrifuged arterial blood samples taken in heparinized capillary tubes. Hb content was determined spectrophotometrically from a single drop of blood (B-Hemoglobin, Hemocue, Stockholm, Sweden). The methemoglobin (MetHb) level was measured via the cyanomethemoglobin method [52]. Arterial blood was collected in heparinized glass capillaries and immediately analyzed for $P_aO_2$, $P_aCO_2$, base excess (BE), and pH (Blood Chemistry Analyzer 248, Bayer, Norwood, Mass.). The comparatively low $P_aO_2$ and high $P_aCO_2$ of these animals are a consequence of their adaptation to a fossorial environment.

Plasma nitrate. Blood samples were collected from carotid artery catheter and centrifuged to separate RBCs and plasma. Plasma proteins were removed by adding equivolume of methanol, and centrifuged at 15000 rpm for 10 min at 4° C. Concentration of nitrate in the supernatant were measured with a NOx analyzer (ENO-20; Eicom, Kyoto, Japan). This analyzer combines Griess method and high-performance liquid chromatography.

Microvascular experimental setup: The unanesthetized animal was placed in a restraining tube with a longitudinal slit from which the window chamber protruded, and then fixed to the microscopic stage of a transillumination intra-vital microscope (BX51WI, Olympus, New Hyde Park, N.Y.). The animals were given 20 min to adjust to the change in the tube environment before measurements. The tissue image was projected onto a CCD camera (COHU 4815) connected to a video recorder and viewed on a monitor. Measurements were carried out using a 40× (LUMPFL-WIR, numerical aperture 0.8, Olympus) water immersion objective. Microhemodynamic measurements were compared to baseline levels obtained before the experimental procedure. The same vessels and functional capillary fields were followed so that direct comparisons to their baseline levels could be performed allowing for more robust statistics for small sample populations.

Microhemodynamics: Arteriolar and venular blood flow velocities were measured online by using the photodiode cross-correlation method (Photo Diode/Velocity Tracker Model 102B, Vista Electronics, San Diego, Calif.). The measured centerline velocity was corrected according to vessel size to obtain the mean RBC velocity (V). A video image-shearing method was used to measure vessel diameter (D). Blood flow (Q) was calculated from the measured values as $Q=\pi \times V \times (D/2)^2$. Changes in arteriolar and venular diameter from baseline were used as indicators of a change in vascular tone. This calculation assumes a parabolic velocity profile and has been found to be applicable to tubes of 15-80 μm internal diameters and for Hcts in the range of 6-60%.

Data analysis: Results are presented as mean standard deviation. Data within each group were analyzed using analysis of variance for repeated measurements (ANOVA, Kruskal-Wallis test). When appropriate, post hoc analyses were performed with the Dunn multiple comparison test. All statistics were calculated using GraphPad Prism 4.01 (GraphPad Software, Inc., San Diego, Calif.). Changes were considered statistically significant if P<0.05.

Anti-bacterial Activity Studies with NAC-SNO-np

Methicillin resistant *Staphylococcus aureus* (MRSA), *E. coli, K Pneumoniae*, and *P. aeruginosa*, Clinical Isolates: All clinical isolates used were collected from Montefiore Medical Center, Bronx, N.Y. All samples were obtained with written consent of all patients according to the practices and standards of the institutional review boards at the Albert Einstein College of Medicine and Montefiore Medical Center. A total of 19 clinical isolates were studied including 4 MRSA, 5 *E. coli*, 5 *K. penumoniae*, and 5 *P. aeruginosa*. All strains were stored in Tryptic Soy Broth (TSB, MP Biomedicals, LLC, Solon, Ohio) containing 40% glycerol at −80° C. until use, and then grown in TSB broth overnight at 37° C. with rotary shaking at 150 r.p.m.

Susceptibility of MRSA, *E. coli, K Pneumoniae*, and *P. aeruginosa* to NAC-SNO-Np-2: To determine the impact of the NAC-SNO-np-2 on the various clinical isolates, TSB was inoculated with a fresh colony of bacteria grown on tryptic soy agar (TSA) plates and suspended in 1 ml of medium. A bacterial suspension of 1 μL was transferred to a 100-well honeycomb plate with 199 μL of TSB per well containing 10 mg/ml NAC-SNO-np-2. Prior to plating, the particles were sonicated for 1 minute on ice with a Fisher sonic Dismembrator (model 200, Fisher Scientific, Pittsburgh, Pa.). Controls included wells containing bacteria with TSB alone. The background OD of nanoparticles was accounted for by plating wells containing TSB and NAC-SNO-np-2 or Np alone. Bacteria and nanoparticles were incubated for 24 hours at 37° C. and growth was assessed at an optical density (OD) of 600 nm every 30 minutes using a micropalate reader (Bioscreen C, Growth Curves USA, Piscataway, N.J.).

Colony Forming Unit (CFU) Assay: After incubation with NAC-SNO-np-2, 10 μL of suspension containing bacteria was aspirated from each experimental group and transferred to an eppendorf tube with 990 ml of phosphate-buffered saline (PBS) and vortexed gently. The suspensions were serially diluted in PBS and aliquots were plated on TSA plates. The percentage of CFU survival was determined by comparing survival of NAC-SNO-np-2 treated bacterial cells relative to the survival of untreated bacteria. Minimum inhibitory concentration required to inhibit the growth of 90% of organisms ($MIC_{90}$) was determined using CFU assays as previously described.

Statistical Analysis: All data were subjected to statistical analysis using GraphPad Prism 5.0 (GraphPad Software, La Jolla, Calif.). P-values were calculated by analysis of variance and were adjusted by use of the Bonferroni correction. P-values of <0.05 were considered significant.

Results

Preparation of SNO-np: The TMOS-based nanoparticle platform employed to generate the SNO/NAC-SNO-np is based on incorporating the molecules of interest into a sol-gel. Typically the TMOS based sol-gels have sufficiently large "pores/channels" to allow for rapid release of any small molecule. Sustained slow release is achieved by filling the pores with structural biopolymers such as chitosan that can form a strong glass-like hydrogen bonding network with elements of the sol-gel polymeric network. The release of "trapped" small molecules occurs when water enters the nanoparticle and starts to slowly disrupt the hydrogen bonding network allowing sustained release of the molecules [53]. Typically, these sol-gels are prepared by adding hydrolyzed TMOS to 50 mM phosphate buffer, pH 7.4, containing all the components to be enclosed. The basic components of NO-np are nitrite, glucose, chitosan and PEG. The compositions of sol-gel preparations are shown in Table 1. For the synthesis of SNO-np, sulfhydryl groups were incorporated within the gel matrix using MPTS which was covalently incorporated into the sol-gel polymeric network. The amount of MPTS to be used was limited by its interference with the polymerization of TMOS into sol-gel. The amount of TMOS and MPTS used was based on maximizing the amount of incorporated thiols without interfering with the polymerization of TMOS. The nitrite concentration was chosen to generate maximum amount of S-nitrosothiols without leaving an excess of unreacted nitrite. Hydrolyzed MPTS and nitrite were added to a cocktail containing other components of the matrix at pH 3. Immediately, hydrolyzed TMOS was added. A sol-gel is formed as a result of condensation and polymerization reaction of TMOS. The gel immediately turned pink indicating the formation of S-nitrosothiols (SNO). The gel formed in the preparation of NO-np, without the addition of MPTS, was translucent and colorless. The gel was dried and ball milled into particles as described in methods section. The gel/particles were shielded from light, throughout.

Preparation of NAC-SNO-np: NAC-SNO was generated from a mixture of N-acetyl-L-cysteine and nitrite in the preparation of NAC-SNO-np. Three types of NAC-SNO-np were prepared using the same amount of N-acetyl-L-cysteine and varying amounts of nitrite as shown in Table 1. The amount of nitrite used for NAC-SNO-np-2 was comparable to that used for SNO-np. At this concentration of nitrite (0.225 M) and N-acetyl-L-cysteine (0.28 M), all the nitrite was expected to be utilized in the formation of NAC-SNO. NAC-SNO-np-1 and NAC-SNO-np-3 received the same amount of N-acetyl-L-cysteine (0.28 M) but with 50% and 200% the amount of nitrite used to prepare NAC-SNO-np-2, respectively. Thus NAC-SNO-np-3 was anticipated to release both NAC-SNO and NO.

All the components of the matrix, except hydrolyzed TMOS, were mixed in 50 mM phosphate, pH 7.4. The pH of the mixture dropped to about 3 after adding N-acetyl-L-cysteine. The cocktail instantly turned red due to the formation of NAC-SNO. Hydrolyzed TMOS was added to incorporate NAC-SNO into a sol-gel. A red gel was formed after 24 h incubation that was subsequently dried and ball milled into fine powder. The gel/powder was protected from light and the powder was stored at −80° C. for longer life of SNO.

Release of SNO/NAC-SNO nanoparticle payloads: Nanoparticles were suspended in 0.5 mM DTPA/PBS and their released payloads (extracts) were analyzed by RPHPLC (FIGS. 1A, B, and C). The only detectable species in the extracts of SNO-np was nitrite (FIG. 1B). Although an excess of sulfhydryl concentration over nitrite was used in the preparation of SNO-np, significant amount of unreacted nitrite was detected in the extract of SNO-np. However, the size of this nitrite peak was ~30% smaller than the corresponding peak in the extract from NO-np (FIG. 1A). This suggests that all the MPTS added was not incorporated into the gel and/or not all of the sulfhydryl groups in the matrix were derivatized to SNO. The ratio of MPTS to TMOS used in the preparation of SNO-np (Table 1) was at the limit in terms of MPTS concentration. Higher amounts of MPTS prevented TMOS polymerization into a sol-gel.

Figure 1C:
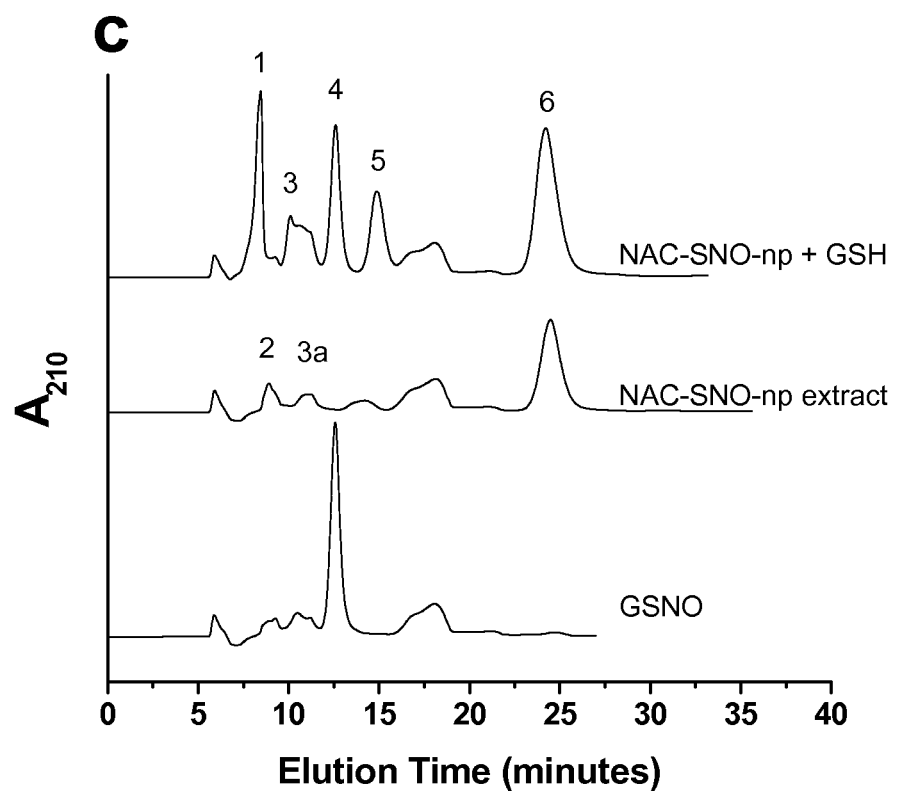

NAC-SNO-np-2 extract contained an insignificant amount of nitrite and no peak corresponding to N-acetyl-L-cysteine was observed (FIG. 1C). Additional peaks corresponding to nitrate, NAC-SNO and non-characterized oxidized products of NAC-SNO were detected. RPHPLC analysis of NAC-SNO-np extract monitored at 335 nm displayed only peak 6 (data not shown). This product was determined to be NAC-SNO.

Production of GSNO from a mixture of GSH and SNO/NAC-SNO-np: Nanoparticles were incubated in 0.5 mM DTPA/PBS, pH 7.4, in the presence of GSH and the reaction mixtures were analyzed by RPHPLC (FIGS. 1 A, B, and C). The reaction mixture of SNO-np (20 mg/ml) and GSH (20 mM) after 1 h incubation demonstrated four peaks in the chromatogram corresponding to unreacted GSH, unreacted nitrite, and the products, GSSG (dimer of GSH) and GSNO (FIG. 1B). Similar results were obtained with NO-np (FIG. 1A). NAC-SNO-np-2 mixed with GSH also displayed a peak corresponding to GSNO (FIG. 1C) that was more prominent than those appearing in the chromatograms of NO-np and SNO-np. Additional peaks representing oxidized products of GSH and NAC-SNO were also present.

Figure 2:
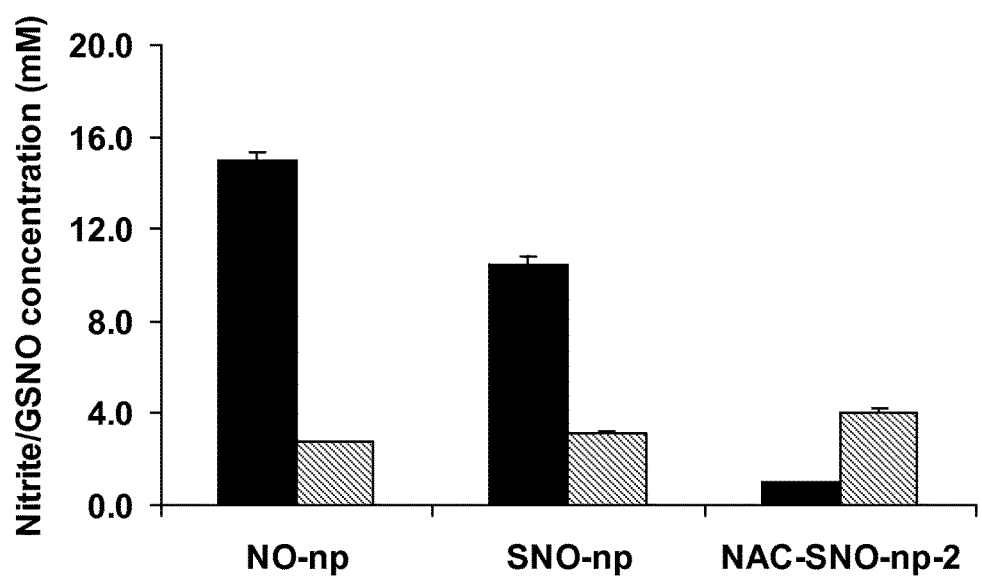
FIG. 2. Comparison of GSNO production from nanoparticles. Amount of nitrite released (filled bars) or GSNO formed (striped bars) when nanoparticles (20 mg/ml) were incubated in DTPA/PBS (pH 7.4) at room temperature for 1 hour in the absence or presence of GSH (20 mM), respectively. NO-np released the highest amount of nitrite and formed the least amount of GSNO with GSH. These results were opposite with NAC-SNO-np-2, indicating higher efficiency of NAC-SNO to form GSNO by S-transnitrosation.

The amount of GSNO produced by these particles after 1 h incubation with GSH is shown in FIG. 2. SNO-np (3.08 mM) and NO-np (2.74 mM) formed comparable amounts of GSNO. Since SNO-np extract released 70% less nitrite as compared to that of NO-np, transnitrosation by SNO-np must be responsible for the 30% higher amount of GSNO formation. NAC-SNO-np-2 produced significantly higher amount of GSNO (4.04 mM) as compared to both NO-np and SNO-np. NAC-SNO-np-2 extract contained negligible amount of nitrite and produced at least 50% more GSNO. Although the same amount of nitrite was used in all these three preparations, NAC-SNO-np-2 produced the largest amount of GSNO, indicating transnitrosation is the major pathway of GSNO formation.

Effect of concentration of NO/SNO-np and GSH on GSNO production: The dose dependent production of GSNO was evaluated varying the concentration of NO/SNO-np at a constant NO/SNO-np and GSH ratio. No GSNO was detected after 1 hour incubation of NO-np or SNO-np at 5 and 10 mg/ml with 5 and 10 mM GSH, respectively (Table 2). However, NAC-SNO-np-2 produced detectable amounts of GSNO at all the concentrations tested. NO-np and SNO-np are capable of generating detectable amount of GSNO only at higher concentrations (20 mg/ml). At higher concentrations (20 mg/ml), the particles were incubated with 20 mM GSH, which reduced the pH of the incubation mixture to approximately pH 5.0; an acidic pH that may have promoted the GSNO production from NO-np and SNO-np.

Figure 3:
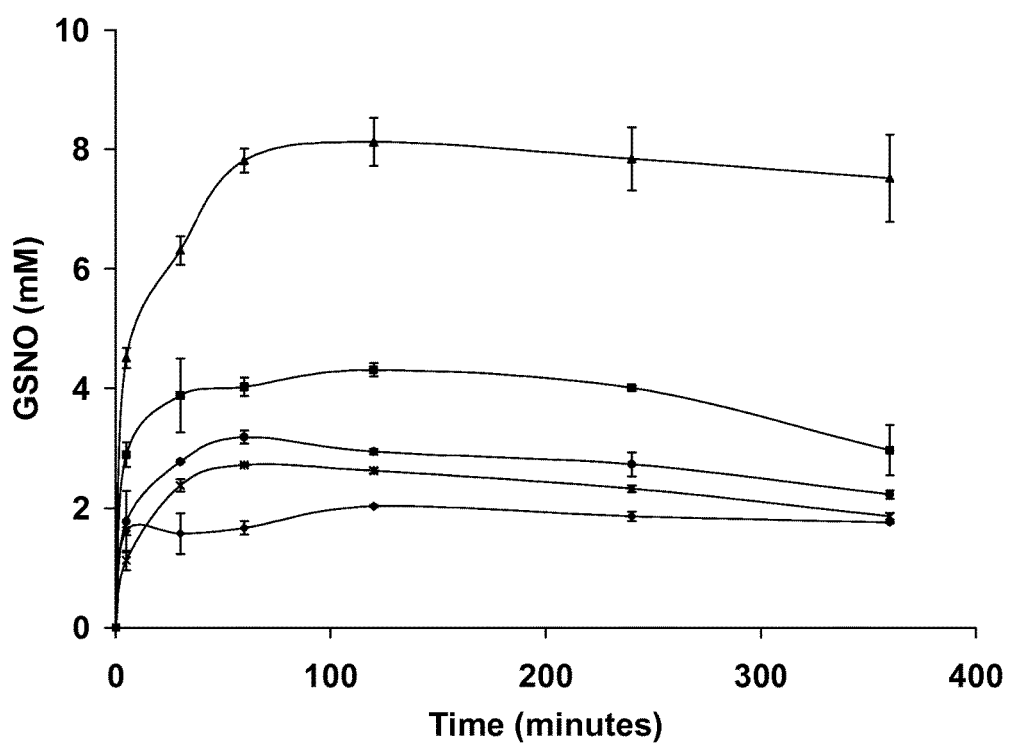
FIG. 3. Time course of GSNO production from a mixture of nanoparticles and GSH. NO-np (*), SNO-np (●), NAC-SNO-np-1 (♦), NAC-SNO-np-2 (■), and NAC-SNO-np-3 (▲) (20 mg/ml) were incubated with GSH (20 mM) in 0.5 mM DTPA/PBS, pH 7.4, at room temperature. Aliquots were taken at time intervals, 50× diluted and analyzed by RPHPLC as described in methods. GSNO concentrations were calculated from the peak areas. Values are the averages of duplicate experiments. In spite of using the same amount of nitrite, NAC-SNO-np-2 formed more GSNO and at a higher rate than NO-np and SNO-np. The rate and amount of GSNO formed from the three formulations of NAC-SNO-np were proportional to the amount of nitrite used in the preparation of these particles. These results demonstrate the highest S-nitrosation efficiency of NAC-SNO-np.

Kinetics of GSNO production by NO/SNO-np in the presence of GSH: One of the most pronounced benefits of the hydrogel-based nanoparticle platform used in this study is its capability of maintaining a sustained release of its payload over a number of hours [53]. A time course of the production of GSNO by the SNO/NAC-SNO-np (20 mg/ml) in the presence of GSH (20 mM) was carried out (FIG. 3). Maximum levels of GSNO were reached in one hour with NO-np and SNO-np samples, producing 2.74 mM and 3.08 mM, respectively, on average. Interestingly, maximum levels of GSNO were not reached with NAC-SNO-np-2 until the two hour time point, indicating a longer sustained release of NAC-SNO from the particles. The overall amount of GSNO formed by this sample (at 2 hours) was significantly higher (4.19 mM) than that formed by NO-np and SNO-np (Table 3).

The other two formulations of NAC-SNO-np, NAC-SNO-np-1 and NAC-SNO-np-3 also required approximately two hours to release the maximum amounts of enclosed components and form the highest levels of GSNO (FIG. 3). The initial rates of GSNO formation as well as the concentrations of GSNO formed were proportional to the initial nitrite concentrations used in the preparation of NAC-SNO-nps. On average NAC-SNO-np-1 through NAC-SNO-np-3 produced 2.01 mM, 4.19 mM, and 7.72 mM GSNO, respectively. The percentage of conversion of nitrite/SNO to GSNO was higher for all the NAC-SNO-np formulations as compared to NO-np or SNO-np (Table 3). The nitrite concentration used in the preparation of NAC-SNO-np-1 was only 50% of that used for NO-np, and more importantly all encapsulated nitrite was utilized for the formation of NAC-SNO. The amount of GSNO formed from NAC-SNO-np-1 was comparable to that formed from NO-np, indicating higher efficiency of S-nitrosation by the SNO motif.

The GSNO concentration in the reaction mixtures of all subtypes of nps started declining after two hours incubation, due to the oxidation of GSNO (FIG. 3). After 24 h, the GSNO level in NAC-SNO-np-3 sample decayed the most (92%) and in NAC-SNO-np-2 decayed the least (37%) (Table 3).

Figure 4:
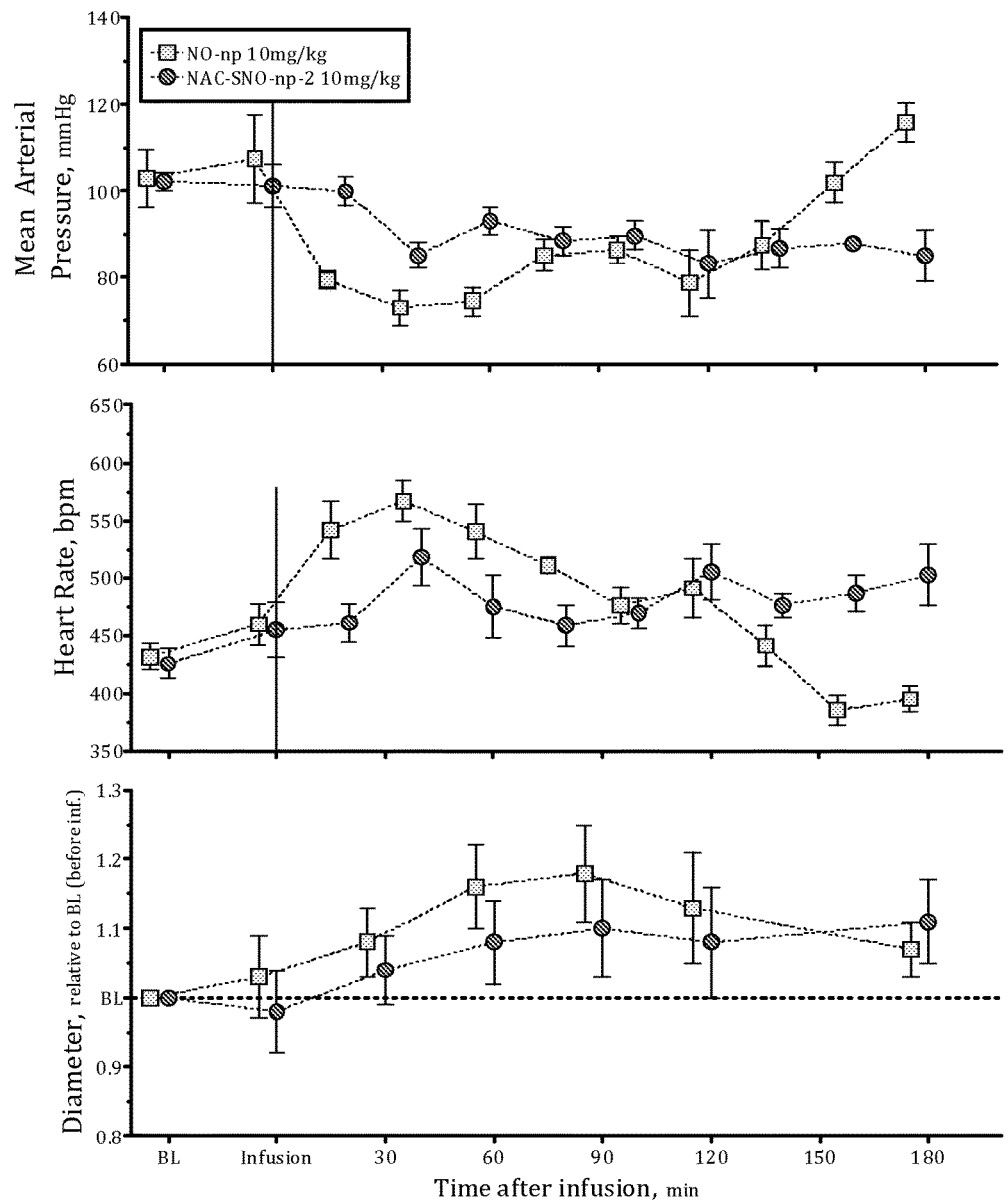
FIG. 4. Vasodilatory effect of NO-np and NAC-SNO-np-2. Infusion of 10 mg/kg of NO-np and NAC-SNO-np-2 in hamsters reduced the mean arterial pressure and heart rate and increased vessel diameter. These changes induced by NAC-SNO-np-2 were lower but longer than NO-np. The effect of NO-np started diminishing after 2 h of infusion. NAC-SNO-np-2 maintained the effect until the termination of the experiment (3 h).

Vasodilatory influence of NO-Np and NAC-SNO-np-2: NO-np and NAC-SNO-np-2 when infused reduced the MAP and increased the heart rate from baseline (FIG. 4). These changes were associated with increased blood vessels diameter (FIG. 4).

Figure 5:
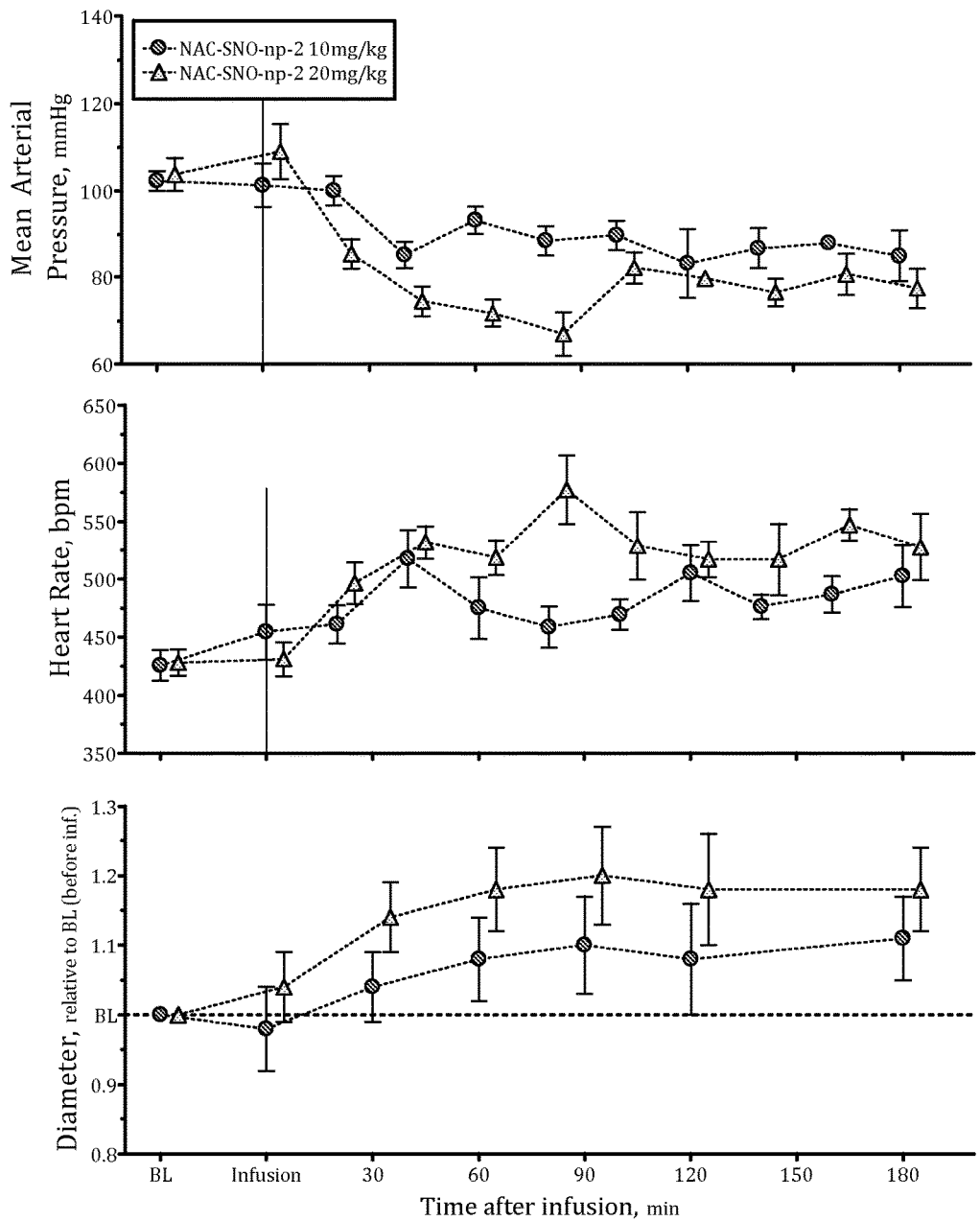
FIG. 5. Dose dependent vasodilatory effect of NAC-SNO-np-2. Infusion of 10 and 20 mg/kg of NAC-SNO-np-2 in hamsters reduced the mean arterial pressure and heart rate and increased vessel diameter in a dose dependent fashion. Dose effects were more pronounce in microvessel diameter compared to systemic hemodynamics, suggesting specific vascular action on peripheral circulation.

NAC-SNO-np-2 effects in MAP, HR and blood vessels diameter increased in a dose dependent manner (FIG. 5), establishing the vasodilatory effect of NAC-SNO-np-2. The magnitudes of these systemic responses to NAC-SNO-np-2 were lower than appreciated with the NO-nps at the lowest concentration tested (10 mg/kgbw). However, the effect of the NO-np on mean arterial pressure began to diminish two hours following intravenous infusion, while NAC-SNO-np-2 maintained these systemic parameters for a longer period, extending to the duration of the experiment (3 hours). These results demonstrate the long lasting vasodilatory effect of NAC-SNO-np-2. The extended impact is likely due to a greater degree of sustained release of NAC-SNO-np and/or NO from the particles compared to the release profiles for the other nanoparticle platforms. MetHb after infusion of NAC-SNO-np-2 were not different compared to NO-np concentrations tested (Table 4). The low levels of MetHb for NAC-SNO-np-2 indicates that the NAC-SNO-np-2 minimally reduces Hb oxygen carrying capacity and suggest significant potential to increase oxygen transport by increasing blood flow via vasodilation. NAC-SNO-np-2 infusion did not increase serum nitrate levels as compared to the NO-nps. Additionally, NAC-SNO-np-2 did not affect blood gas parameter in terms of $P_aO_2$ and $P_aCO_2$ compared to NO-nps. The NO released from the NO-np increased the ratio of $P_aO_2$ to the fraction of inspired oxygen concentration. The release of exogenous NO form the NO-np retains the advantages of NO as a selective pulmonary vasodilator, but at the same time may have the disadvantages of gaseous NO as a therapeutic agent, such as rebound pulmonary hypertension. In contrast, intravenous NAC-SNO-np-2 had minor effects in the ratio of $P_aO_2$ to the fraction of inspired oxygen concentration. This suggests that NAC-SNO-np-2 has limited effects on pulmonary vasculature or preferentially act on the larger conducting airways as compared with the smallest airways (changes of the latter contribute to changes in compliance and gas exchange). Additionally, the limited effect in pulmonary vasculature of NAC-SNO-np may prevent the rebound pulmonary hypertension of free NO therapies.

Figure 6A:
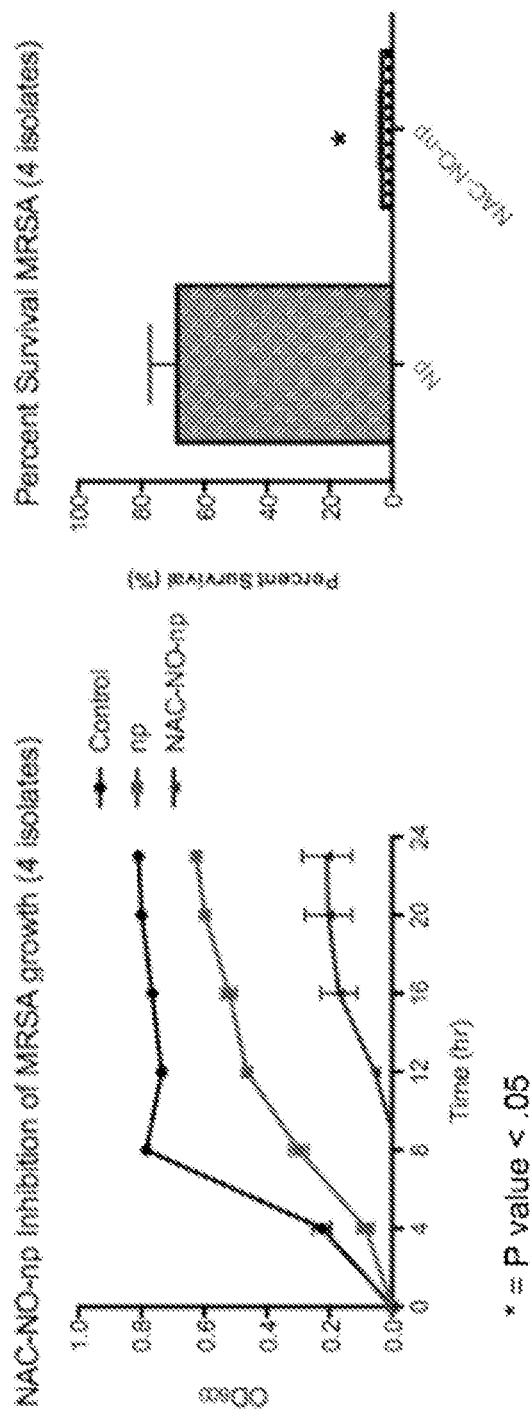
FIG. 6A-6D. Anti-bacterial activity of NAC-SNO-np-2. Susceptibility of MRSA (A), $P.$ $aeruginosa$ (B), $K.$ $pneumoniae$ (C), and $E.$ $coli$ (D) to NAC-SNO-np-2 (10 mg/ml) and empty nanoparticles (np; 10 mg/ml) was investigated by real-time Bioscreen analysis and percent survival determined by colony forming unit assays following 24 hours incubation. The data shown are an average of the results from the bacterial isolates tested in triplicates and error bars represent standard error from mean. Each point in figures in left panels represents the average of four measurements of four identical wells and error bars denote standard error from mean, Experiments were repeated in triplicate and performed at least twice on separate days. Asterisks denote p value significance (* P<0.05) calculated by unpaired two-tailed t test analysis. The growth of MRSA growth was completely inhibited for approximately 10 hours, with only 3.46% cell survival following 24 hours of co-incubation with NAC-NO-np-2. The growth of $P.$ $aeruginosa$ and $K.$ $pneumoniae$ was also inhibited for several hours. $E.$ $Coli$ was less susceptible to NAC-NO-np-2.
Figure 6B:
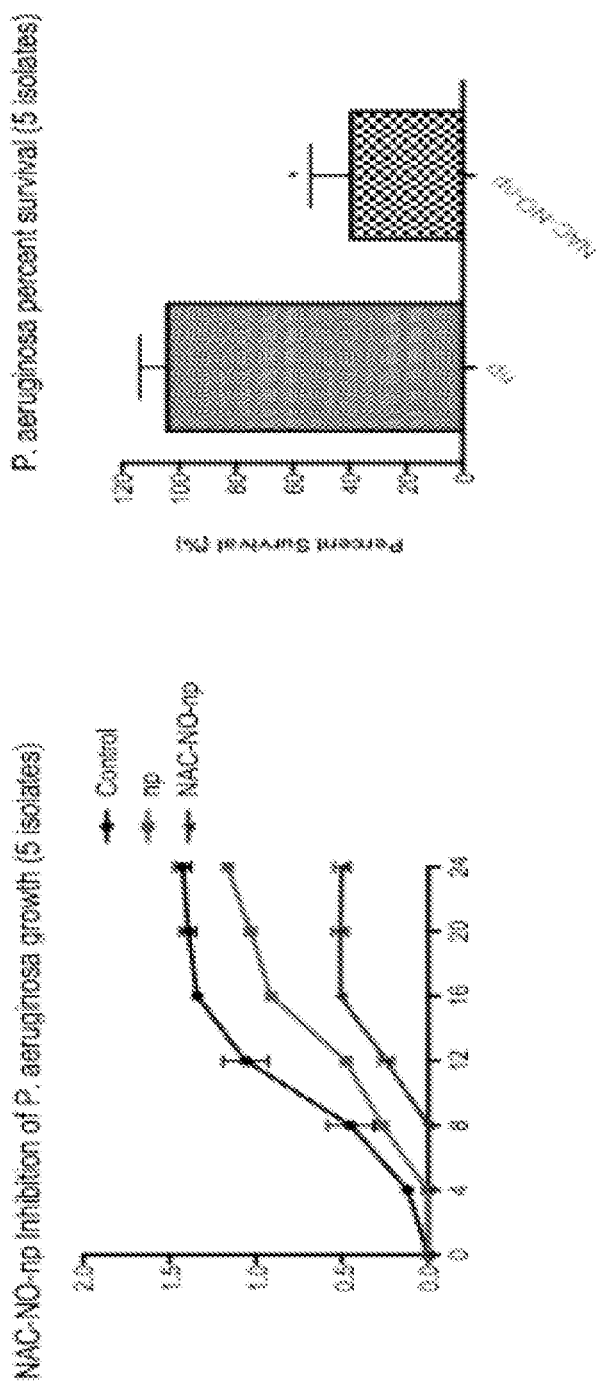
Figure 6C:
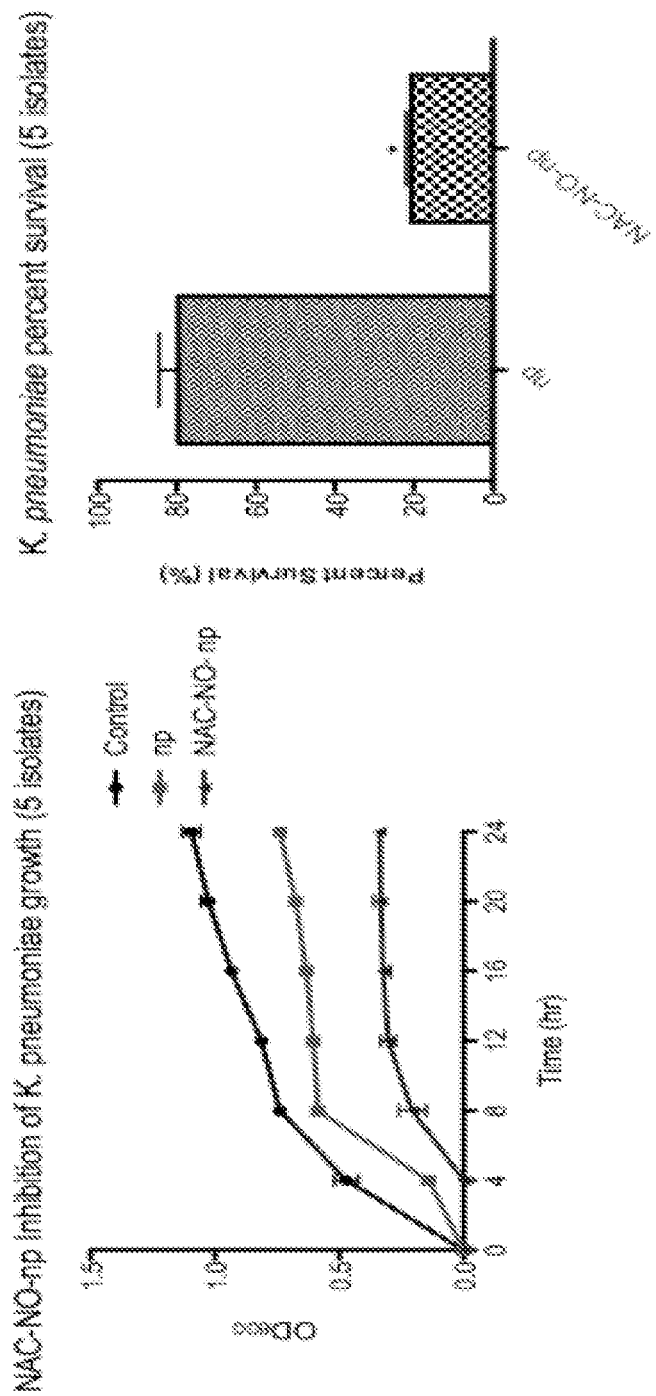
Figure 6D:
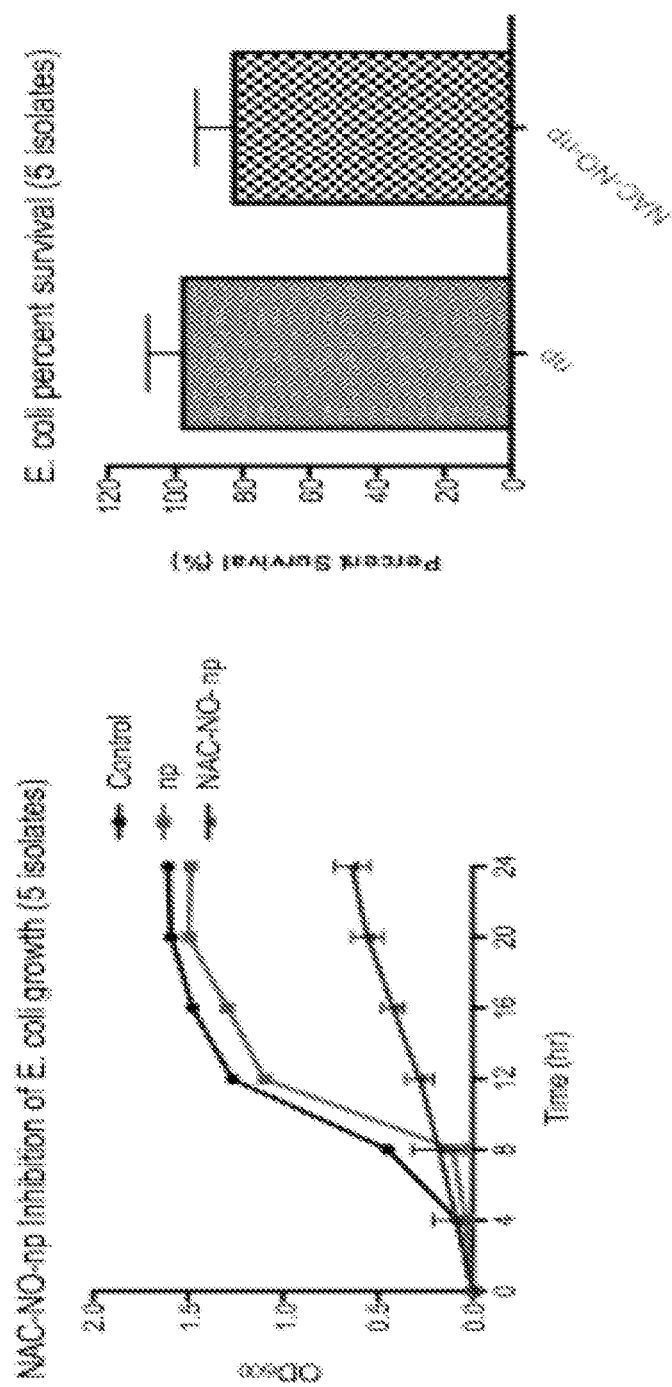

Anti-bacterial activity studies with NAC-SNO-np and Cap-SNO-np: The bioactivity of NAC-SNO-np-2 on drug resistant bacteria has also been evaluated. The growth of MRSA, P. aeruginosa, K. pneumoniae and E. coli was monitored in the presence of NAC-SNO-np-2 for 24 h by Bioscreen C analysis. MRSA growth was completely inhibited for up to 10 hours, with only 3.46% cell survival following 24 hours of co-incubation with the NAC-SNO-np-2 (FIG. 6A). The growth of P. aeruginosa and K. pneumoniae was also inhibited completely for 8 and 4 hours, respectively, by NAC-SNO-np-2. The cell survival was about 40 and 20%, respectively after 24 hours incubation (FIGS. 6B & C). E. coli was less susceptible to NAC-SNO-np-2 (FIG. 6D) as compared to the other bacteria described above. Although the rate of the growth of E. coli was reduced by these np, the cell survival after 24 hours was not significantly altered as compared to the control.

Figure 7A:
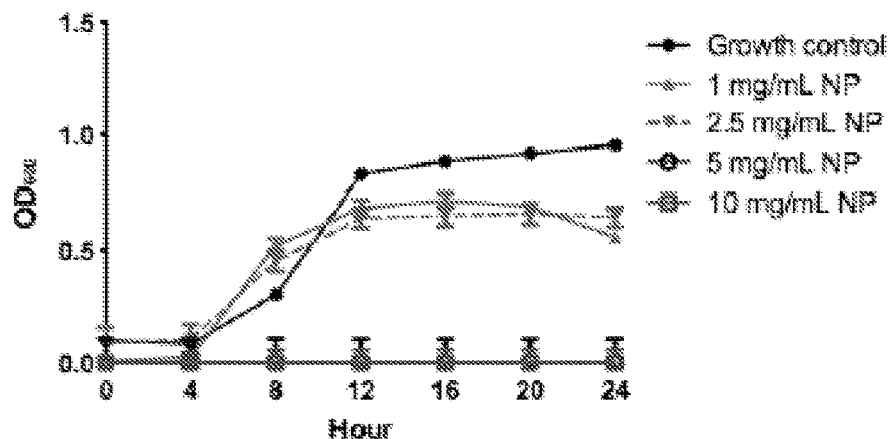
FIG. 7A-7C. Anti-bacterial activity of Captopril(Cap)-SNO-np. Susceptibility of MRSA (A) and $E.$ $coli$ (B, C) to Cap-SNO-np was investigated as described for FIG. 6. The growth of MRSA and $E.$ $coli$ was completely inhibited for at least 24 hours by Cap-SNO-np at the concentrations 5 and 10 mg/ml, respectively. The bactericidal effect of Cap-SNO-np against these two strains is much higher than that of NAC-SNO-np. (D) Data from 5 isolates.
Figure 7B:
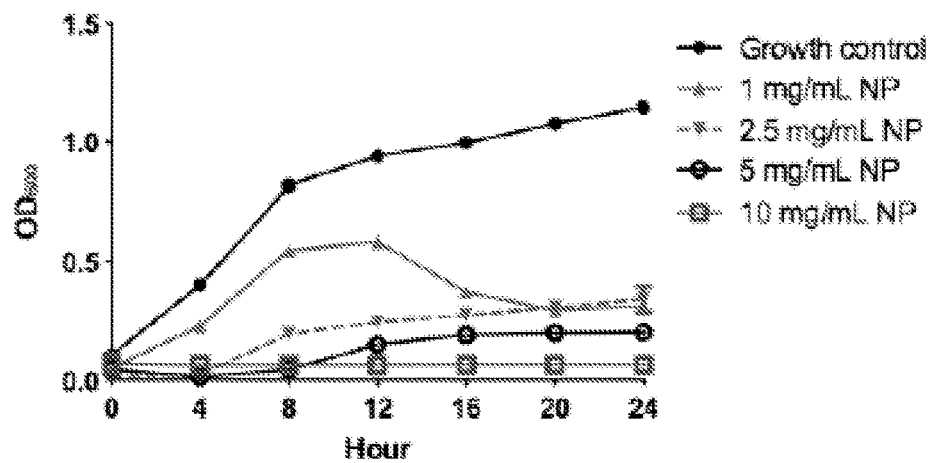
Figure 7C:
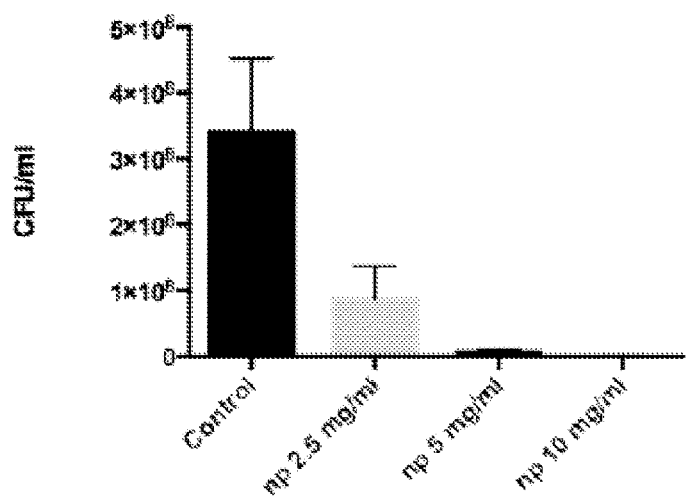

Susceptibility of MRSA (FIG. 7A) and E. coli (FIGS. 7B,C) to Cap-SNO-np was also investigated. The growth of MRSA and E. coli was completely inhibited for at least 24 hours by Cap-SNO-np at the concentrations 5 and 10 mg/ml, respectively. The bactericidal effect of Cap-SNO-np against these two strains is much higher than that of NAC-SNO-np.

Discussion

The physiological influence of NO is exerted predominantly through the posttranslational modification and functional regulation of proteins. The interaction of NO with soluble guanylyl cyclase (sGC) and generation of cyclic guanosine monophosphate (cGMP) was previously described to be the major pathway for the biological effects of NO [54]. However, evidence is also emerging for cGMP-independent biological influence of NO. The cGMP-independent pathways of NO effects are predicted to be mediated by S-nitrosylation of cysteine thiols of various proteins [55; 56; 57; 58; 59; 60; 61; 62]. Unlike the cGMP-dependent influence of NO that solely relies on protein kinase G, cGMP-independent mechanisms are regulated by S-nitrosylation and denitrosylation of various proteins involved and account for a wide range of NO-mediated functions.

RSNOs are capable of activating sGC and induce accumulation of cGMP [44; 63; 64]. This must be mediated by the NO released from RSNO. However, no co-relation was noticed between biological effects of RSNOs and the rate of NO released and/or cGMP accumulation, in several studies [45; 63; 65; 66; 67]. RSNOs have also been known to exert biological effects that are independent of sGC, including cGMP-independent vasodilation [56; 68], anti-platelet effects [63; 69] and alterations in enzyme function and regulation of ion channels and receptors. Since RSNOs are highly capable transnitrosation agents, cGMP-independent pathways could play major role in the biological effects of these molecules. The lack of co-relation of rates of NO release and biological effects of RSNOs indicate that transfer of other derivatives of NO such as NO+ to a protein thiol (S-nitrosylation) may account for several of these actions [70; 71].

S-nitrosation of various proteins has been implicated in physiological processes, including vasodilation, antimicrobial activity and other NO mediated cellular functions [15; 39; 43; 47; 55; 72]. Hypo- or hyper-S-nitrosylation of specific protein targets have been linked to human diseases, such as disorders of the cardiovascular, musculoskeletal and nervous systems [36; 37; 55]. In mouse models, genetic ablation of 5-nitrosoglutathione reductase, the enzyme principally responsible for GSNO metabolism, results in enhanced levels of SNO-proteins and significantly attenuates experimental asthma and heart failure models [36]. The Cys-SNO residues identified in in vivo proteins/enzymes are located in their catalytic sites and may indicate a physiological role for S-nitrosation of the enzymes [36].

RSNO-based therapeutics can be considered more efficient than NO-based therapeutics due to their capacity for long lasting release of NO as well as a more facile transnitrosating capability. In a study involving contraction of isolated arteries, SNO based NO donors have been shown to induce longer-lasting vasodilation than other types of NO donors tested [73]. Unlike many NO-therapeutics based on pro-drugs, RSNO-therapeutics do not need any activation to exhibit transnitrosation activity; transnitrosation by RSNOs occurs at physiological conditions [34; 43; 45].

NAC-SNO and GSNO have been tested in humans as therapeutics for different clinical conditions. Topical application of NAC-SNO inhibited the contraction frequency and basal pressure of the sphincter of Oddi, and reduced duodenal motility in patients undergoing endoscopic retrograde cholangiopancreatography (ERCP) and biliary manometry [74]. GSNO was shown to exhibit anti-thrombotic effects in healthy human subjects without inducing hypotension when infused at low doses [75; 76]. Intracoronary infusion of GSNO during coronary balloon angioplasty prevented the angioplasty-induced increase in platelet expression of P-selection and glycoprotein IIb/IIIa, without altering blood pressure [77]. GSNO infusion in women with severe preeclampsia reduced maternal mean arterial pressure, platelet activation, and uterine artery resistance, without further compromise of fetal Doppler indices [78].

In the present study, the long lasting effect of RSNOs was further extended by enclosing/conjugating RSNO to sustained-releasing hydrogel-based particles. Although all three formulations, NO-np, SNO-np and NAC-SNO-np-2 are capable of producing GSNO from GSH, NAC-SNO-np-2 was found to be the most potent S-nitrosating agent. NAC-SNO-np-2 is capable of producing greater concentrations of GSNO at lower (physiological) concentrations of GSH, which elicited longer lasting biological impacts as compared to NO-np and SNO-np. NAC-SNO-np-2 not only produced more GSNO but stabilized GSNO for extended periods (at least 24 hours) within medium in vitro. This feature is likely to be very significant for GSNO based therapeutic formulations for topical applications (antimicrobial and wound healing etc).

In a Syrian hamster animal model, NO-np induced vasodilation more rapidly than NAC-SNO-np-2. However, although the vascular impact of NAC-SNO-np-2 was more gradual, it was longer lasting. These results are consistent with the previous observations on the differential influence of SNO-based and NO-based NO donors on the relaxation of isolated arteries [73]. Isolated arteries exposed to SNO-based drugs and subsequently washed were found to be less contracted in response to norepinephrine as compared to controls; NO-based drugs however could not confer similar protection from norepinephrine induced contraction. S-nitrosation of arterial tissue proteins by SNO-based drugs was suggested as a possible source of NO storage to induce long lasting vasodilation.

In addition, NAC-SNO has been shown to induce hypotension more effectively than sodium nitroprusside (SNP) in normal and acute hypertension induced rats [15]. SNP is currently in use to treat malignant hypertension in emergency settings and cardiac failure [79; 80]. The vascular effect of NAC-SNO (~9 min) was much longer than that of SNP (~1 min) NAC-SNO-np-2 in the current study maintained a decrease in MAP in hamsters for several hours, establishing the enhanced benefits of nanoparticle based formulation for sustained release of NAC-SNO for therapeutic applications.

NO-np inhibits growth of a variety of drug-resistant bacteria. This anti-bacterial activity of NO-np is enhanced in the presence of GSH, which co-relates with GSNO formation in this system. The present study demonstrates the anti-bacterial activity of NAC-SNO-np-2 against the same bacterial species that have been tested with NO-np. Interestingly, the level of impact of NAC-SNO-np-2 (without GSH) on bacterial growth was comparable to that of NO-np in the presence of GSH. The nitrite/SNO concentration (0.225 M) of NAC-SNO-np-2 is four-fold lower than that was used in the preparation of NO-np (0.9 M) in the previous study. The concentration of NAC-SNO-np-2 (10 mg/ml) used in the anti-microbial experiments was two-fold higher than that of NO-np (5 mg/ml). Thus, NAC-SNO-np-2 is at least two-fold more efficient than NO-np. The anti-microbial activity of NO has been implicated to be mediated by S-nitrosation and transnitrosation (RSNO drugs-2 and 42-46). NAC-SNO-np-2, being a more potent S-nitrosating/transnitrosating agent than NO-np, acts as a better anti-bacterial agent than NO-np and bypasses the need of adding GSH for enhanced anti-bacterial activity. Since NAC-SNO is more stable than GSNO, a long lasting therapeutic can be formulated from NAC-SNO-np.

Three types of NAC-SNO-np were formulated using different concentrations of nitrite and a constant amount of N-acetyl-L-cysteine (Table 1) to determine the contribution of NO/SNO towards S-nitrosation. Based on the total nitrite/SNO concentrations contained, all the three formulations of NAC-SNO-np generated more GSNO as compared to NO-np (Table 3). Importantly, although NAC-SNO-np-1 was made with only 50% amount of nitrite as compared to NO-np and was not found to release any unreacted nitrite, these particles generated analogous concentrations of GSNO to NO-np. These results clearly indicate that 5-transnitrosation by NAC-SNO is a more efficient approach to form RSNO or S-nitrosothiols on proteins than simply by nitrite/NO mediated S-nitrosylation.

The composition of NAC-SNO-np-3 is similar to 1:1 combination of NAC-SNO-np-2 (in terms of SNO) and NO-np (in terms of NO). Along these lines, the amount of GSNO generated by NAC-SNO-np-3 was also comparable to the sum of that generated by the other two formulations. NAC-SNO-np-3 is expected to exert vasodilatory effects in vivo along the lines of a combination of the effects seen with NO-np (immediate effect) and NAC-SNO-np-2 (long lasting effect). Additionally, NAC-SNO-np-3 is advantageous over a combination of NO-np and NAC-SNO-np-2 since it would use only 50% of the particles. The amount of particles that must be infused is a critical factor for in vivo applications.

Although NAC-SNO-np-3 produced more GSNO than NAC-SNO-np-2, at the end of 24 h NAC-SNO-np-2 retained more GSNO than NAC-SNO-np-3. This feature makes NAC-SNO-np-2 a practical NO/GSNO based therapeutic for topical applications such as wound healing, anti-microbial, and erectile dysfunction treatment.

In the present studies, the formation of GSNO from GSH was used as a model reaction to evaluate the transnitrosating efficiency of the nanoparticle formulations. The relative efficiencies of the formulations may be extended to the transnitrosation of protein thiols. NAC-SNO-np formulations can make efficient therapeutics in physiological processes involving S-nitrosation of protein thiols. In addition to NAC-SNO, other RSNOs such as SNO-captopril can also make a good candidate for nanoparticle based delivery. Captopril is an angiotensin-converting enzyme (ACE) inhibitor and is used for hypertension. SNO-captopril is a transnitrosating agent and [81; 82] has been shown to control acute and chronic hypertensive effects more efficiently than captopril in rats [83; 84].

The hydrogel-based nanoparticle platform that has been employed in the present study is comprised of N-acetyl-L-cysteine, nitrite, glucose, chitosan, PEG 400 and a silica backbone, all of which have been shown previously to be non-toxic [25]. RSNO based therapeutics do not appear to induce tolerance in animals. Nanoparticle based sustained release of RSNOs provides an approach to enhance their stability in vivo and achieve long lasting therapeutic effects.

TABLE 1

Nanoparticle formulations.

| Sample | [Nitrite] (M) | [D-glucose] (M) | [N-Ac-Cys] (M) | [Hydrolyzed MPTS] (M) | [Hydrolyzed TMOS] M) | [Nitrite]:[Thiol] | Theoretical nitrite or SNO per mg of dry np (micromoles) |
|---|---|---|---|---|---|---|---|
| NO-np | 0.225 | 0.055 | N/A | N/A | 0.68 | N/A | 0.75 (nitrite) |
| SNO-np | 0.225 | 0.055 | N/A | 0.28 | 0.68 | 1:1.2 | 0.75 (SNO) |
| NAC-SNO-np-1 | 0.113 | 0.0275 | 0.28 | N/A | 0.68 | 1:2.5 | 0.375 (SNO) |
| NAC-SNO-np-2 | 0.225 | 0.055 | 0.28 | N/A | 0.68 | 1:1.25 | 0.75 (SNO) |
| NAC-SNO-np-3 | 0.450 | 0.110 | 0.28 | N/A | 0.68 | 1:0.625 | 1.50 (nitrite + SNO) |

TABLE 2

GSNO production is dependent on Np and GSH concentration.

| Sample | Np (mg/ml) | Theoretical [nitrite] and/or [SNO] (mM) | [GSH] (mM) | [GSNO]* (mM) |
|---|---|---|---|---|
| NO-np | 5 | 3.75 | 5 | ND |
| " | 10 | 7.50 | 10 | ND |
| " | 20 | 15.00 | 20 | 2.74 |

TABLE 2-continued

GSNO production is dependent on Np and GSH concentration.

| Sample | Np (mg/ml) | Theoretical [nitrite] and/or [SNO] (mM) | [GSH] (mM) | [GSNO]* (mM) |
|---|---|---|---|---|
| SNO-np | 5 | 3.75 | 5 | ND |
| " | 10 | 7.50 | 10 | ND |
| " | 20 | 15.00 | 20 | 3.08 |
| NAC-SNO-np-2 | 5 | 3.75 | 5 | 1.19 |
| " | 10 | 7.50 | 10 | 1.60 |
| " | 20 | 15.00 | 20 | 4.04 |

*GSNO formed after 1 hour incubation of Np with GSH in DTPA/PBS
ND = no GSNO peak was detected by RPHPLC

TABLE 3

Maximum GSNO formed from Np formulations.

| Sample | t MAX GSNO* (min) | [GSNO] (mM) | Percentage of nitrite/SNO converted to GSNO | [GSNO] after 24 h (mM) | Percentage of GSNO remained after 24 h |
|---|---|---|---|---|---|
| NO-np | 60 | 2.74 (15)# | 18 | 1.38 | 50 |
| SNO-np | 60 | 3.08 (15) | 20 | 0.76 | 25 |
| NAC-SNO-np-1 | 120 | 2.01 (7.5) | 27 | 1.00 | 50 |
| NAC-SNO-np-2 | 120 | 4.19 (15) | 28 | 2.66 | 63 |
| NAC-SNO-np-3 | 120 | 7.72 (30) | 26 | 0.75 | 8 |

*Time at which maximum GSNO formed from np (20 mg/ml) and GSH (20 mM).
The values in parentheses represent the initial concentration of nitrite and/or SNO of Nps
GSNO concentrations are the average of duplicate experiments.

TABLE 4

Blood chemistry.

| | NO-np | | | NAC-SNO-np-2 | | |
|---|---|---|---|---|---|---|
| | Baseline | | | | | |
| | | 10 mg/kg$_{BW}$ | | 10 mg/kg$_{BW}$ | | 20 mg/kg$_{BW}$ |
| | | Time after infusion, min | | | | |
| | 60 | 180 | 60 | 180 | 60 | 180 |
| MetHb, % | -0- | -0- | 5 ± 2 | -0- | 3 ± 2 | -0- | 7 ± 3 |
| $NO_3^-$, μM | 1.3 ± 0.3 | 2.8 ± 0.9 † | 3.2 ± 0.8 † | 1.6 ± 0.4 †‡ | 1.7 ± 0.4 † | 1.8 ± 0.5 † | 2.0 ± 0.8 † |
| $p_aO_2$, mmHg | 57.6 ± 7.6 | 76.2 ± 7.2 † | 73.1 ± 6.7 † | 59.3 ± 7.7 †‡ | 58.4 ± 6.2 †‡ | 62.4 ± 7.1 † | 64.1 ± 7.2 † |
| $p_aCO_2$, mmHg | 51.5 ± 5.6 | 47.8 ± 6.8 † | 47.7 ± 5.8 † | 49.2 ± 6.7 ‡ | 49.8 ± 7.1 ‡ | 47.5 ± 6.3 | 46.5 ± 4.7 |

Values are means ± SD.
Baseline included all the animals.
MetHb, fraction of Total Hb converted to Methemoglobin;
$NO_3^-$, Nitrate;
$P_aO_2$, arterial partial $O_2$ pressure;
$P_aCO_2$, arterial partial pressure of $CO_2$.
†, P < 0.05 compared to Baseline;
‡, P < 0.05 compared to NO-np at same concentration.

REFERENCES

[1] A. R. Butler, F. W. Flitney, and D. L. Williams, NO, nitrosonium ions, nitroxide ions, nitrosothiols and iron-nitrosyls in biology: a chemist's perspective. Trends Pharmacol Sci 16 (1995) 18-22.
[2] K. A. Hanafy, J. S. Krumenacker, and F. Murad, NO, nitrotyrosine, and cyclic GMP in signal transduction. Med Sci Monit 7 (2001) 801-19.
[3] L. J. McDonald, and F. Murad, Nitric oxide and cyclic GMP signaling. Proc Soc Exp Biol Med 211 (1996) 1-6.
[4] M. W. Radomski, R. M. Palmer, and S. Moncada, Comparative pharmacology of endothelium-derived relaxing factor, nitric oxide and prostacyclin in platelets. Br J Pharmacol 92 (1987) 181-7.
[5] M. A. Marletta, P. S. Yoon, R. Iyengar, C. D. Leaf, and J. S. Wishnok, Macrophage oxidation of L-arginine to nitrite and nitrate: nitric oxide is an intermediate. Biochemistry 27 (1988) 8706-11.
[6] J. B. Hibbs, Jr., R. R. Taintor, Z. Vavrin, and E. M. Rachlin, Nitric oxide: a cytotoxic activated macrophage effector molecule. Biochem Biophys Res Commun 157 (1988) 87-94.
[7] D. J. Stuehr, S. S. Gross, I. Sakuma, R. Levi, and C. F. Nathan, Activated murine macrophages secrete a metabolite of arginine with the bioactivity of endothelium-derived relaxing factor and the chemical reactivity of nitric oxide. J Exp Med 169 (1989) 1011-20.
[8] C. P. de Oliveira, F. I. Simplicio, V. M. de Lima, K. Yuahasi, F. P. Lopasso, V. A. Alves, D. S. Abdalla, F. J. Carrilho, F. R. Laurindo, and M. G. de Oliveira, Oral administration of S-nitroso-N-acetylcysteine prevents the onset of non alcoholic fatty liver disease in rats. World J Gastroenterol 12 (2006) 1905-11.
[9] H. Rubbo, V. Darley-Usmar, and B. A. Freeman, Nitric oxide regulation of tissue free radical injury. Chem Res Toxicol 9 (1996)809-20.
[10] S. R. Jaffrey, and S. H. Snyder, Nitric oxide: a neural messenger. Annu Rev Cell Dev Biol 11 (1995) 417-40.
[11] A. Friedman, and J. Friedman, New biomaterials for the sustained release of nitric oxide: past, present and future. Expert Opinion on Drug Delivery 6 (2009) 1113-1122.
[12] G. R. Thatcher, An introduction to NO-related therapeutic agents. Curr Top Med Chem 5 (2005) 597-601.
[13] P. J. Henry, O. H. Drummer, and J. D. Horowitz, S-nitrosothiols as vasodilators: implications regarding tolerance to nitric oxide-containing vasodilators. Br J Pharmacol 98 (1989) 757-66.
[14] E. A. Kowaluk, R. Poliszczuk, and H. L. Fung, Tolerance to relaxation in rat aorta: comparison of an S-nitrosothiol with nitroglycerin. Eur J Pharmacol 144 (1987) 379-83.
[15] K. F. Ricardo, S. M. Shishido, M. G. de Oliveira, and M. H. Krieger, Characterization of the hypotensive effect of S-nitroso-N-acetylcysteine in normotensive and hypertensive conscious rats. Nitric Oxide 7 (2002) 57-66.

[16] J. N. Bates, M. T. Baker, R. Guerra, Jr., and D. G. Harrison, Nitric oxide generation from nitroprusside by vascular tissue. Evidence that reduction of the nitroprusside anion and cyanide loss are required. Biochem Pharmacol 42Suppl (1991) S157-65.

[17] A. R. Butler, C. Glidewell, J. McGinnis, and W. I. Bisset, Further investigations regarding the toxicity of sodium nitroprusside. Clin Chem 33 (1987) 490-2.

[18] G. Hagan, and J. Pepke-Zaba, Pulmonary hypertension, nitric oxide and nitric oxide-releasing compounds. Expert Rev Respir Med 5 163-71.

[19] A. R. Butler, and P. Rhodes, Chemistry, analysis, and biological roles of S-nitrosothiols. Anal Biochem 249 (1997) 1-9.

[20] C. F. Lam, S. Sviri, K. F. Ilett, and P. V. van Heerden, Inhaled diazeniumdiolates (NONOates) as selective pulmonary vasodilators. Expert Opin Investig Drugs 11 (2002) 897-909.

[21] C. M. Maragos, D. Morley, D. A. Wink, T. M. Dunams, J. E. Saavedra, A. Hoffman, A. A. Bove, L. Isaac, J. A. Hrabie, and L. K. Keefer, Complexes of .NO with nucleophiles as agents for the controlled biological release of nitric oxide. Vasorelaxant effects. J Med Chem 34 (1991) 3242-7.

[22] C. M. Maragos, J. M. Wang, J. A. Hrabie, J. J. Oppenheim, and L. K. Keefer, Nitric oxide/nucleophile complexes inhibit the in vitro proliferation of A375 melanoma cells via nitric oxide release. Cancer Res 53 (1993) 564-8.

[23] A. J. Friedman, G. Han, M. S. Navati, M. Chacko, L. Gunther, A. Alfieri, and J. M. Friedman, Sustained release nitric oxide releasing nanoparticles: characterization of a novel delivery platform based on nitrite containing hydrogel/glass composites. Nitric Oxide 19 (2008) 12-20.

[24] G. Han, A. J. Friedman, and J. M. Friedman, Nitric oxide releasing nanoparticle synthesis and characterization. Methods Mol Biol 704 (2011) 187-95.

[25] P. Cabrales, G. Han, C. Roche, P. Nacharaju, A. J. Friedman, and J. M. Friedman, Sustained release nitric oxide from long-lived circulating nanoparticles. Free Radic Biol Med 49 (2010) 530-8.

[26] P. Cabrales, G. Han, P. Nacharaju, A. J. Friedman, and J. M. Friedman, Reversal of hemoglobin-induced vasoconstriction with sustained release of nitric oxide. Am J Physiol Heart Circ Physiol 300 (2011) H49-56.

[27] G. Han, M. Tar, D. S. Kuppam, A. Friedman, A. Melman, J. Friedman, and K. P. Davies, Nanoparticles as a novel delivery vehicle for therapeutics targeting erectile dysfunction. J Sex Med 7 (2010) 224-33.

[28] A. Friedman, K. Blecher, D. Sanchez, C. Tuckman-Vernon, P. Gialanella, J. M. Friedman, L. R. Martinez, and J. D. Nosanchuk, Susceptibility of Gram-positive and -negative bacteria to novel nitric oxide-releasing nanoparticle technology. Virulence 2 (2011) 217-21.

[29] A. J. Friedman, K. Blecher, D. Schairer, C. Tuckman-Vernon, P. Nacharaju, D. Sanchez, P. Gialanella, L. R. Martinez, J. M. Friedman, and J. D. Nosanchuk, Improved antimicrobial efficacy with nitric oxide releasing nanoparticle generated S-nitrosoglutathione. Nitric Oxide 25 (2011) 381-6.

[30] G. Han, L. R. Martinez, M. R. Mihu, A. J. Friedman, J. M. Friedman, and J. D. Nosanchuk, Nitric oxide releasing nanoparticles are therapeutic for *Staphylococcus aureus* abscesses in a murine model of infection. PLoS One 4 (2009) e7804.

[31] M. R. Mihu, U. Sandkovsky, G. Han, J. M. Friedman, J. D. Nosanchuk, and L. R. Martinez, The use of nitric oxide releasing nanoparticles as a treatment against Acinetobacter baumannii in wound infections. Virulence 1 (2010) 62-7.

[32] L. R. Martinez, G. Han, M. Chacko, M. R. Mihu, M. Jacobson, P. Gialanella, A. J. Friedman, J. D. Nosanchuk, and J. M. Friedman, Antimicrobial and healing efficacy of sustained release nitric oxide nanoparticles against *Staphylococcus aureus* skin infection. J Invest Dermatol 129 (2009) 2463-9.

[33] D. Schairer, L. Martinez, K. Blecher, J. Chouake, P. Nacharaju, P. Gialanella, J. M. Friedman, J. Nosanchuk, and A. Friedman, Nitric oxide nanoparticles: Pre-clinical utility as a therapeutic for intramuscular abscesses. Virulence 3 (2012).

[34] H. H. Al-Sa'doni, and A. Ferro, S-nitrosothiols as nitric oxide-donors: chemistry, biology and possible future therapeutic applications. Curr Med Chem 11 (2004) 2679-90.

[35] D. L. Diesen, D. T. Hess, and J. S. Stamler, Hypoxic vasodilation by red blood cells: evidence for an s-nitrosothiol-based signal. Circ Res 103 (2008) 545-53.

[36] M. W. Foster, D. T. Hess, and J. S. Stamler, Protein S-nitrosylation in health and disease: a current perspective. Trends Mol Med 15 (2009) 391-404.

[37] M. W. Foster, T. J. McMahon, and J. S. Stamler, S-nitrosylation in health and disease. Trends Mol Med 9 (2003) 160-8.

[38] D. Giustarini, A. Milzani, R. Colombo, I. Dalle-Donne, and R. Rossi, Nitric oxide and S- nitrosothiols in human blood. Clin Chim Acta 330 (2003) 85-98.

[39] J. S. Stamler, D. I. Simon, J. A. Osborne, M. E. Mullins, O. Jaraki, T. Michel, D. J. Singel, and J. Loscalzo, S-nitrosylation of proteins with nitric oxide: synthesis and characterization of biologically active compounds. Proc Natl Acad Sci U S A 89 (1992) 444-8.

[40] I. Hornyak, K. Marosi, L. Kiss, P. Grof, and Z. Lacza, Increased stability of S-nitrosothiol solutions via pH modulations. Free Radic Res.

[41] T. M. Hu, and T. C. Chou, The kinetics of thiol-mediated decomposition of S-nitrosothiols. Aaps J 8 (2006) E485-92.

[42] L. Grossi, and P. C. Montevecchi, A kinetic study of S-nitrosothiol decomposition. Chemistry 8 (2002) 380-7.

[43] G. Richardson, and N. Benjamin, Potential therapeutic uses for S-nitrosothiols. Clin Sci (Lond) 102 (2002) 99-105.

[44] B. T. Mellion, L. J. Ignarro, C. B. Myers, E. H. Ohlstein, B. A. Ballot, A. L. Hyman, and P. J. Kadowitz, Inhibition of human platelet aggregation by S-nitrosothiols. Heme-dependent activation of soluble guanylate cyclase and stimulation of cyclic GMP accumulation. Mol Pharmacol 23 (1983) 653-64.

[45] H. Al-Sa'doni, and A. Ferro, S-Nitrosothiols: a class of nitric oxide-donor drugs. Clin Sci (Lond) 98 (2000) 507-20.

[46] H. H. Al-Sa'doni, I. Y. Khan, L. Poston, I. Fisher, and A. Ferro, A novel family of S-nitrosothiols: chemical synthesis and biological actions. Nitric Oxide 4 (2000) 550-60.

[47] L. J. Ignarro, H. Lippton, J. C. Edwards, W. H. Baricos, A. L. Hyman, P. J. Kadowitz, and C. A. Gruetter, Mechanism of vascular smooth muscle relaxation by organic nitrates, nitrites, nitroprusside and nitric oxide: evidence for the involvement of S-nitrosothiols as active intermediates. J Pharmacol Exp Ther 218 (1981) 739-49.

[48] M. H. Krieger, K. F. Santos, S. M. Shishido, A. C. Wanschel, H. F. Estrela, L. Santos, M. G. De Oliveira, K. G. Franchini, R. C. Spadari-Bratfisch, and F. R. Laurindo, Antiatherogenic effects of S-nitroso-N-acetylcysteine in hypercholesterolemic LDL receptor knockout mice. Nitric Oxide 14 (2006) 12-20.

[49] J. A. Garcia, L. dos Santos, A. L. Moura, K. F. Ricardo, A. C. Wanschel, S. M. Shishido, R. C. Spadari-Bratfisch, H. P. de Souza, and M. H. Krieger, S-nitroso-N-acetyl-cysteine (SNAC) prevents myocardial alterations in hypercholesterolemic LDL receptor knockout mice by antiinflammatory action. J Cardiovasc Pharmacol 51 (2008) 78-85.

[50] P. Nachuraju, A. J. Friedman, J. M. Friedman, and P. Cabrales, Exogenous nitric oxide prevents cardiovascular collapse during hemorrhagic shock. Resuscitation 82 (2011) 607-13.

[51] A. Colantuoni, S. Bertuglia, and M. Intaglietta, Quantitation of rhythmic diameter changes in arterial microcirculation. Am J Physiol 246 (1984) H508-H517.

[52] M. Sakata, A. Yoshida, and M. Haga, Methemoglobin in blood as determined by double-wavelength spectrophotometry. Clin Chem 28 (1982) 508-11.

[53] A. J. Friedman, G. Han, M. S. Navati, M. Chacko, L. Gunther, A. Alfieri, and J. M. Friedman, Sustained release nitric oxide releasing nanoparticles: Characterization of a novel delivery platform based on nitrite containing hydrogel/glass composites. Nitric Oxide-Biology and Chemistry 19 (2008) 12-20.

[54] F. Murad, Cyclic guanosine monophosphate as a mediator of vasodilation. J Clin Invest 78 (1986) 1-5.

[55] B. Lima, M. T. Forrester, D. T. Hess, and J. S. Stamler, S-nitrosylation in cardiovascular signaling. Circ Res 106 (2010) 633-46.

[56] J. C. Wanstall, K. L. Homer, and S. A. Doggrell, Evidence for, and importance of, cGMP-independent mechanisms with NO and NO donors on blood vessels and platelets. Curr Vasc Pharmacol 3 (2005) 41-53.

[57] A. M. Hamad, A. Clayton, B. Islam, and A. J. Knox, Guanylyl cyclases, nitric oxide, natriuretic peptides, and airway smooth muscle function. Am J Physiol Lung Cell Mol Physiol 285 (2003) L973-83.

[58] G. P. Ahern, V. A. Klyachko, and M. B. Jackson, cGMP and S-nitrosylation: two routes for modulation of neuronal excitability by NO. Trends Neurosci 25 (2002)510-7.

[59] B. Brune, S. Mohr, and U. K. Messmer, Protein thiol modification and apoptotic cell death as cGMP-independent nitric oxide (NO) signaling pathways. Rev Physiol Biochem Pharmacol 127 (1996) 1-30.

[60] F. Murad, Nitric oxide and cyclic guanosine monophosphate signaling in the eye. Can J Ophthalmol 43 (2008) 291-4.

[61] G. Boerrigter, H. Lapp, and J. C. Burnett, Modulation of cGMP in heart failure: a new therapeutic paradigm. Handb Exp Pharmacol (2009) 485-506.

[62] N. Hogg, The biochemistry and physiology of S-nitrosothiols. Annu Rev Pharmacol Toxicol 42 (2002) 585-600.

[63] M. P. Gordge, J. S. Hothersall, and A. A. Noronha-Dutra, Evidence for a cyclic GMP-independent mechanism in the anti-platelet action of S-nitrosoglutathione. Br J Pharmacol 124 (1998) 141-8.

[64] I. S. Severina, O. G. Bussygina, N. V. Pyatakova, I. V. Malenkova, and A. F. Vanin, Activation of soluble guanylate cyclase by NO donors—S-nitrosothiols, and dinitrosyl-iron complexes with thiol-containing ligands. Nitric Oxide 8 (2003) 155-63.

[65] A. R. Butler, H. H. Al-Sa'doni, I. L. Megson, and F. W. Flitney, Synthesis, decomposition, and vasodilator action of some new S-nitrosated dipeptides. Nitric Oxide 2 (1998) 193-202.

[66] E. A. Kowaluk, and H. L. Fung, Spontaneous liberation of nitric oxide cannot account for in vitro vascular relaxation by S-nitrosothiols. J Pharmacol Exp Ther 255 (1990) 1256-64.

[67] W. R. Mathews, and S. W. Kerr, Biological activity of S-nitrosothiols: the role of nitric oxide. J Pharmacol Exp Ther 267 (1993) 1529-37.

[68] V. S. Fernandes, A. Martinez-Saenz, P. Recio, A. S. Ribeiro, A. Sanchez, M. P. Martinez, A. C. Martinez, A. Garcia-Sacristan, L. M. Orensanz, D. Prieto, and M. Hernandez, Mechanisms involved in the nitric oxide-induced vasorelaxation in porcine prostatic small arteries. Naunyn Schmiedebergs Arch Pharmacol 384 (2011) 245-53.

[69] R. Priora, A. Margaritis, S. Frosali, L. Coppo, D. Summa, D. Di Giuseppe, C. Aldinucci, G. Pessina, A. Di Stefano, and P. Di Simplicio, In vitro inhibition of human and rat platelets by NO donors, nitrosoglutathione, sodium nitroprusside and SIN-1, through activation of cGMP-independent pathways. Pharmacol Res 64 (2011) 289-97.

[70] J. S. Stamler, S-nitrosothiols and the bioregulatory actions of nitrogen oxides through reactions with thiol groups. Curr Top Microbiol Immunol 196 (1995) 19-36.

[71] D. R. Arnelle, and J. S. Stamler, NO+, NO, and NO− donation by S-nitrosothiols: implications for regulation of physiological functions by S-nitrosylation and acceleration of disulfide formation. Arch Biochem Biophys 318 (1995) 279-85.

[72] D. T. Hess, A. Matsumoto, S. O. Kim, H. E. Marshall, and J. S. Stamler, Protein S-nitrosylation: purview and parameters. Nat Rev Mol Cell Biol 6 (2005) 150-66.

[73] J. L. Alencar, I. Lobysheva, K. Chalupsky, M. Geffard, F. Nepveu, J. C. Stoclet, and B. Muller, S-nitrosating nitric oxide donors induce long-lasting inhibition of contraction in isolated arteries. J Pharmacol Exp Ther 307 (2003) 152-9.

[74] A. Slivka, R. Chuttani, D. L. Carr-Locke, L. Kobzik, D.S. Bredt, J. Loscalzo, and J. S. Stamler, Inhibition of sphincter of Oddi function by the nitric oxide carrier S-nitroso-N-acetylcysteine in rabbits and humans. J Clin Invest 94 (1994) 1792-8.

[75] A. J. de Belder, R. MacAllister, M. W. Radomski, S. Moncada, and P. J. Vallance, Effects of S-nitroso-glutathione in the human forearm circulation: evidence for selective inhibition of platelet activation. Cardiovasc Res 28 (1994) 691-4.

[76] B. Ramsay, M. Radomski, A. De Belder, J. F. Martin, and P. Lopez-Jaramillo, Systemic effects of S-nitrosoglutathione in the human following intravenous infusion. Br J Clin Pharmacol 40 (1995) 101-2.

[77] E. J. Langford, A. S. Brown, R. J. Wainwright, A. J. de Belder, M. R. Thomas, R. E. Smith, M. W. Radomski, J. F. Martin, and S. Moncada, Inhibition of platelet activity by S-nitrosoglutathione during coronary angioplasty. Lancet 344 (1994) 1458-60.

[78] C. Lees, E. Langford, A. S. Brown, A. de Belder, A. Pickles, J. F. Martin, and S. Campbell, The effects of S-nitrosoglutathione on platelet activation, hypertension, and uterine and fetal Doppler in severe preeclampsia. Obstet Gynecol 88 (1996) 14-9.

[79] U. Elkayam, M. Janmohamed, M. Habib, and P. Hatamizadeh, Vasodilators in the management of acute heart failure. Crit Care Med 36 (2008) S95-105.

[80] J. D. Kirk, J. T. Parissis, and G. Filippatos, Pharmacologic stabilization and management of acute heart failure syndromes in the emergency department. Heart Fail Clin 5 (2009) 43-54, vi.

[81] J. W. Park, Dual role of S-nitrosocaptopril as an inhibitor of angiotensin-converting enzyme and a nitroso group carrier. Biochem Biophys Res Commun 189 (1992) 206-10.

[82] T. P. Dasgupta, and D. V. Aquart, Transfer of nitric oxide from nitrovasodilators to free thiols—evidence of two distinct stages. Biochem Biophys Res Commun 335 (2005) 730-3.

[83] L. Jia, and R.C. Blantz, The effects of S-nitrosocaptopril on renal filtration and blood pressure in rats. Eur J Pharmacol 354 (1998) 33-41.

[84] D. Y. Tsui, A. Gambino, and J. C. Wanstall, S-nitrosocaptopril: acute in-vivo pulmonary vasodepressor effects in pulmonary hypertensive rats. J Pharm Pharmacol 55 (2003) 1121-5.

What is claimed is:

1. A method of preparing nanoparticles comprising a S-nitrosothiol containing molecule encapsulated within the nanoparticle, the method comprising:
   a) providing a buffer solution comprising chitosan, polyethylene glycol, nitrite, glucose, and a S-nitrosothiol containing molecule; and
   b) adding hydrolyzed tetramethoxysilane to the buffer solution to produce a sol-gel.

2. The method of claim 1, further comprising:
   c) lyophilizing and ball milling the sol-gel to produce the nanoparticles comprising a S-nitrosothiol containing molecule encapsulated within the nanoparticle.

3. The method of claim 1, wherein the S-nitrosothiol containing molecule encapsulated within the nanoparticle is S-nitroso-N-acetyl cysteine and/or S-nitroso-captopril.

4. The method of claim 1, wherein tetramethoxysilane is hydrolyzed with HCl by sonication on an ice-bath.

5. The method of claim 1, wherein the nanoparticles have a diameter of 10 nm to 100 μm.

6. A nanoparticle produced by the method of claim 1.

7. A method of making a suspension of nanoparticles, wherein the nanoparticles are produced by the method of claim 1, comprising the steps of: suspending the nanoparticles in a diethylenetriaminepenta-acetic acid/phosphate buffered saline mixture; and incubating the nanoparticles in the mixture at room temperature at pH 7.4 for 1 hour so as to make the suspension of nanoparticles.

8. A method of generating S-nitrosoglutathione comprising the steps of: suspending the nanoparticles prepared by the method of claim 1 in a glutathione solution prepared in a diethylenetriaminepenta-acetic acid/phosphate buffered saline mixture; and incubating the nanoparticles in the mixture at room temperature at. pH 7.4 for 1 hour so as to thereby generate S-nitrosoglutathione.

* * * * *